US009200011B2

(12) United States Patent
Van Zandt et al.

(10) Patent No.: US 9,200,011 B2
(45) Date of Patent: Dec. 1, 2015

(54) RING CONSTRAINED ANALOGS AS ARGINASE INHIBITORS

(71) Applicant: Mars, Incorporated, McLean, VA (US)

(72) Inventors: Michael Van Zandt, McLean, VA (US); Gunnar Erik Jagdmann, Jr., McLean, VA (US)

(73) Assignee: Mars, Incorporated, McLean, VA (US)

( * ) Notice: Subject to any disclaimer, the term of this patent is extended or adjusted under 35 U.S.C. 154(b) by 0 days.

(21) Appl. No.: 14/391,901

(22) PCT Filed: Mar. 13, 2013

(86) PCT No.: PCT/US2013/030930
§ 371 (c)(1),
(2) Date: Oct. 10, 2014

(87) PCT Pub. No.: WO2013/158262
PCT Pub. Date: Oct. 24, 2013

(65) Prior Publication Data
US 2015/0080341 A1    Mar. 19, 2015

Related U.S. Application Data

(60) Provisional application No. 61/625,814, filed on Apr. 18, 2012.

(51) Int. Cl.
*C07F 5/02* (2006.01)
*A61K 31/69* (2006.01)
(52) U.S. Cl.
CPC ..................................... *C07F 5/025* (2013.01)
(58) Field of Classification Search
None
See application file for complete search history.

(56) References Cited

U.S. PATENT DOCUMENTS

2012/0129806 A1   5/2012   Van Zandt et al.
2015/0191492 A1   7/2015   Van Zandt et al.

FOREIGN PATENT DOCUMENTS

WO    WO-99/19295 A1      4/1999
WO    WO-2010/085797 A2   7/2010
WO    WO-2011133653 A1    10/2011
WO    WO-2012058065 A1    5/2012

OTHER PUBLICATIONS

U.S. Appl. No. 13/276,806, filed Oct. 2011, Van Zandt, M., et al.*
"International Application Serial No. PCT/US2013/030930, International Search Report mailed May 23, 2013", 3 pgs.
Colleluori, et al., "Classical and Slow-Binding Inhibitors of Human Type II Arginase," Biochemistry, 40(31): 9356-9362 (Jul. 2001).
Kabalka, et al., "Synthesis of a series of boronated unnatural cyclic amino acids as potential boro neutron capture therapy agents," Applied Organometallic Chemistry, 22: 516-522 (2008).
Lei, et al. "Progress of Boronic Acids as Enzyme Inhibitors" Chinese Journal of Pharmaceuticals, 40(3) 213 (2009) (English Abstract only).
International Search Report for PCT/US2011/056844 dated Dec. 14, 2011.
IPRP from PCT/US2013/030930 dated Oct. 30, 2014.

* cited by examiner

*Primary Examiner* — Michael Barker
(74) *Attorney, Agent, or Firm* — Foley Hoag LLP; David P. Halstead

(57) ABSTRACT

The inventive boronic acid analogs are potent inhibitors of Arginase I and II activity. These compounds are candidate therapeutics for treating a disease or disorder associated with an imbalance in the activity or concentration of cellular arginase I and arginase II enzymes. The invention also provides pharmaceutical compositions of the inventive compounds and methods for using the compositions for therapy.

19 Claims, No Drawings

RING CONSTRAINED ANALOGS AS ARGINASE INHIBITORS

CROSS REFERENCE TO RELATED APPLICATIONS

This is a U.S. National Stage Application under 35 U.S.C. 371 of International Application No. PCT/US2013/030930, filed Mar. 13, 2013, published on Oct. 24, 2013 as WO 2013/158262 A1, and that claims the benefit of priority to U.S. Provisional Patent Application No. 61/625,814, filed Apr. 18, 2012, both of which applications are incorporated by reference in their entireties as if fully set forth herein.

BACKGROUND OF THE INVENTION

The present invention relates generally to inhibitors of arginase and their use for the treatment of pathological states. Two isoforms of arginase have been identified to date. Arginase I (ARG I), which is expressed in the cytosole, and Arginase II (ARG II), which is expressed in mitochondria. The arginase enzymes together with the NOS enzymes play an important role in regulating the levels of free arginine in cells.

The arginases are implicated to play a role in various pathological states. These include, for example, erectile dysfunction, pulmonary hypertension, hypertension, atherosclerosis, renal disease, asthma, T-cell dysfunction, ischemia reperfusion injury, neurodegenerative diseases, wound healing, and fibrotic diseases. Although, the mechanism of action of arginase enzymes in these disease states is still a subject of ongoing research, several studies implicate that the arginase enzymes are often upregulated during pathological disease states.

For example, it is postulated that upregulation of arginase activity results in reduced levels of arginine, which in turn reduces the level of NO a physiologically important signaling molecule that is required for cell division, stimulating enhanced blood flow and for controlling muscular and neurological signal transduction.

In addition to its role in regulating NO levels, arginase also effects production of critical polyamines such as putrescine, spermidine and spermine. As arginase consumes arginine it produces ornithine. Ornithine is subsequently converted to putrescine, spermidine and spermine via ornithine decarboxylase, spermidine synthase and spermine synthase respectively. Thus, the arginase enzymes control physiological signaling events by controlling the intracellular levels of polyamine signal transducers. See Wang, J-Y; and Casero, Jr., R. A., Ed; Humana Press, Totowa, N.J., 2006.

These results implicate, therefore, a role for inhibitors of arginase as candidate therapeutics for the treatment of various disease states. The present invention provides compounds as inhibitors of arginase activity, as well as methods for using the inventive compounds in treatment.

SUMMARY OF THE INVENTION

The present invention provides certain boron-containing compounds that are inhibitors of arginase activity. The invention also provides methods for using the inventive compounds in treatment. In one embodiment, therefore, inventive compounds and their pharmaceutically acceptable formulations are provided as therapeutic agents capable of inhibiting arginase activity. Compounds and pharmaceutical formulations in accordance with this invention are useful for treating a number of diseases and conditions, including but not limited to pulmonary hypertension, erectile dysfunction (ED), hypertension, atherosclerosis, renal disease, asthma, T-cell dysfunction, ischemia reperfusion injury, neurodegenerative diseases, wound healing, and fibrotic diseases.

In one embodiment, the invention provides a compound that is selected from the following table:

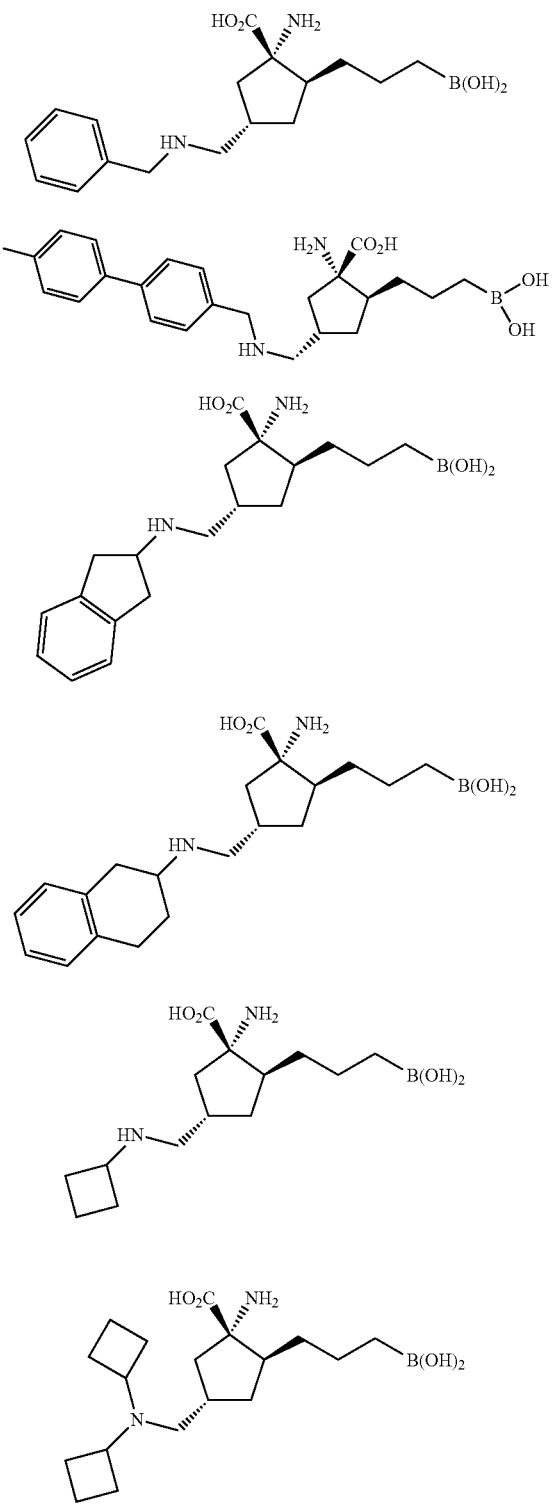

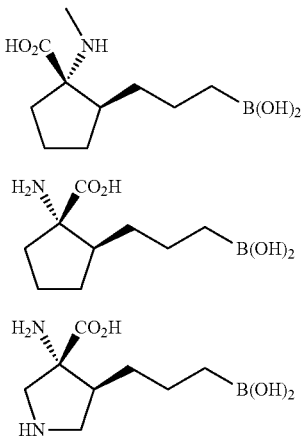

The invention also encompasses pharmaceutically acceptable salts, stereoisomers, tautomers, and prodrugs of such compounds.

In another embodiment invention provides a pharmaceutical composition that comprises a compound that is selected from the above table or pharmaceutically acceptable salts, stereoisomers, tautomers, or a prodrug of the inventive compound and a pharmaceutically acceptable carrier.

The invention also provides in one embodiment a method for inhibiting arginase I, arginase II, or a combination thereof in a cell comprising contacting the cell with at least one compound selected form the above table. Pursuant to another embodiment, the invention provides a method for treating or preventing a disease or a condition associated with expression or activity of arginase I, arginase II, or a combination thereof in a subject, comprising administering to the subject a therapeutically effective amount of at least one compound selected form the above table.

Compounds in accordance with the present invention and their pharmaceutical formulations are also useful for treating a number of disorders, including but not limited to cardiovascular disorders, sexual disorders, wound healing disorders, gastrointestinal disorders, autoimmune disorders, immune disorders, infections, pulmonary disorders, fibrotic disorders and hemolytic disorders.

DETAILED DESCRIPTION

The compounds according to the present invention are inhibitors of arginase I and arginase II activity. Thus, the inventive compounds are candidate therapeutic agents for treating diseases and disorders associated with cellular arginase imbalance.

Compounds of the invention can exist in various isomeric forms, including configurational, geometric, and conformational isomers, including, for example, cis- or trans-conformations. Compounds of the present invention may also exist in one or more tautomeric forms, including both single tautomers and mixtures of tautomers. The term "isomer" is intended to encompass all isomeric forms of a compound of this invention, including tautomeric forms of the compound.

Some of the inventive compounds contain one or more chiral centers. Because of the presence of an asymmetric center, certain compounds according to the present invention can exist as enantiomers and diasteroisomers or mixtures thereof, including racemix mixtures. Optical isomers of the compounds of the invention can be obtained by known techniques such as asymmetric synthesis, chiral chromatography, simulated moving bed technology or via chemical separation of stereoisomers through the employment of optically active resolving agents.

Unless otherwise indicated, "stereoisomer" means one stereoisomer of a compound that is substantially free of other stereoisomers of that compound. Thus, a stereomerically pure compound having one chiral center will be substantially free of the opposite enantiomer of the compound. A stereomerically pure compound having two chiral centers will be substantially free of other diastereomers of the compound. A typical stereomerically pure compound comprises greater than about 80% by weight of one stereoisomer of the compound and less than about 20% by weight of other stereoisomers of the compound, for example greater than about 90% by weight of one stereoisomer of the compound and less than about 10% by weight of the other stereoisomers of the compound, or greater than about 95% by weight of one stereoisomer of the compound and less than about 5% by weight of the other stereoisomers of the compound, or greater than about 97% by weight of one stereoisomer of the compound and less than about 3% by weight of the other stereoisomers of the compound.

If there is a discrepancy between a depicted structure and a name given to that structure, then the depicted structure controls. Additionally, if the stereochemistry of a structure or a portion of a structure is not indicated with, for example, bold or dashed lines, the structure or portion of the structure is to be interpreted as encompassing all stereoisomers of it. In some cases, however, where more than one chiral center exists, the structures and names may be represented as single enantiomers to help describe the relative stereochemistry. Those skilled in the art of organic synthesis will know if the compounds are prepared as single enantiomers from the methods used to prepare them.

A "pharmaceutically acceptable salt" is a pharmaceutically acceptable, organic or inorganic acid or base salt of a compound of the invention. Representative pharmaceutically acceptable salts include, e.g., alkali metal salts, alkali earth salts, ammonium salts, water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. A pharmaceutically acceptable salt can have more than one charged atom in its structure. In this instance the pharmaceutically acceptable salt can have multiple counterions. Thus, a pharmaceutically acceptable salt can have one or more charged atoms and/or one or more counterions.

The terms "treat", "treating" and "treatment" refer to the amelioration or eradication of a disease or symptoms associated with a disease. In certain embodiments, such terms refer to minimizing the spread or worsening of the disease resulting from the administration of one or more prophylactic or therapeutic agents to a patient with such a disease.

The terms "prevent," "preventing," and "prevention" refer to the prevention of the onset, recurrence, or spread of the disease in a patient resulting from the administration of a prophylactic or therapeutic agent.

The term "effective amount" refers to an amount of a compound of the invention, or other active ingredient sufficient to provide a therapeutic or prophylactic benefit in the treatment or prevention of a disease or to delay or minimize symptoms associated with a disease. Further, a therapeutically effective amount with respect to a compound of the invention means that amount of therapeutic agent alone, or in combination with other therapies, that provides a therapeutic benefit in the treatment or prevention of a disease. Used in connection with a compound of the invention, the term can encompass an amount that improves overall therapy, reduces or avoids symptoms or causes of disease, or enhances the therapeutic efficacy of or synergies with another therapeutic agent.

The terms "modulate", "modulation" and the like refer to the ability of an inventive compound to increase or decrease the function, or activity of, for example, Arginase I or Arginase II. "Modulation", in its various forms, is intended to encompass inhibition, antagonism, partial antagonism, activation, agonism and/or partial agonism of the activity associated with arginase. Arginase inhibitors are compounds that, e.g., bind to, partially or totally block stimulation, decrease, prevent, delay activation, inactivate, desensitize, or down regulate signal transduction. The ability of a compound to modulate arginase activity can be demonstrated in an enzymatic assay or a cell-based assay.

A "patient" includes an animal, such as a human, cow, horse, sheep, lamb, pig, chicken, turkey, quail, cat, dog, mouse, rat, rabbit or guinea pig. The animal can be a mammal such as a non-primate and a primate (e.g., monkey and human). In one embodiment, a patient is a human, such as a human infant, child, adolescent or adult.

The term "prodrug" refers to a precursor of a drug that is a compound which upon administration to a patient, must undergo chemical conversion by metabolic processes before becoming an active pharmacological agent. Exemplary prodrugs of compounds in accordance with the present invention are esters, pinenes, dioxaborolanes, and amides.

Inventive Compounds

The present invention provides small molecule therapeutics that are potent inhibitors of arginase I and II activities. Exemplary compounds in accordance with the present invention are shown in Table 1 below. While some exemplary compounds are depicted with stereochemistry, it should be understood that the invention includes all possible stereoisomers, such as diastereomers, of the compounds.

TABLE 1

| Ex.# | Structure* | Name |
| --- | --- | --- |
| 1 | 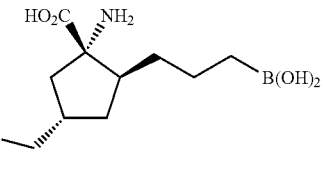 | (1S,2S,4S)-1-amino-4-((benzylamino)methyl)-2-(3-boronopropyl)cyclopentanecarboxylic acid |
| 2 | 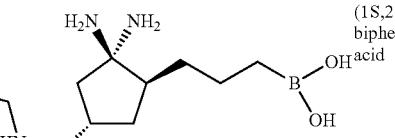 | (1S,2S,4S)-1-amino-2-(3-boronopropyl)-4-((((4'-chloro-[1,1'-biphenyl]-4-yl)methyl)amino)methyl)cyclopentanecarboxylic acid |
| 3 | 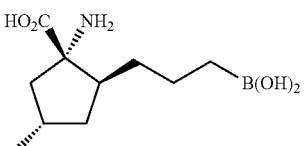 | (1S,2S,4S)-1-amino-2-(3-boronopropyl)-4-((((2,3-dihydro-1H-inden-2-yl)amino)methyl)cyclopentanecarboxylic acid |
| 4 | 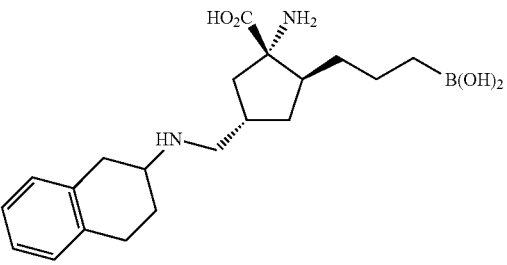 [SMILES: N[C@@]1(C(=O)O)C[C@@H](CNC2CCc3ccccc3C2)C[C@@H]1CCCB(O)O] | (1S,2S,4S)-1-amino-2-(3-boronopropyl)-4-(((1,2,3,4-tetrahydronaphthalen-2-yl)amino)methyl)cyclopentanecarboxylic acid |

TABLE 1-continued

| Ex.# | Structure* | Name |
|---|---|---|
| 5 | 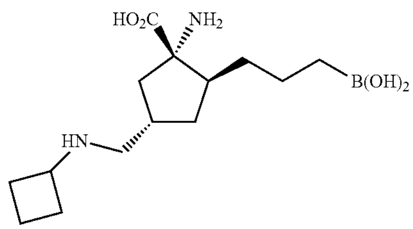 [SMILES: N[C@@]1(C(=O)O)C[C@@H](CNC2CCC2)C[C@@H]1CCCB(O)O] | (1S,2S,4S)-1-amino-2-(3-boronopropyl)-4-((cyclobutylamino)methyl)cyclopentanecarboxylic acid |
| 6 | 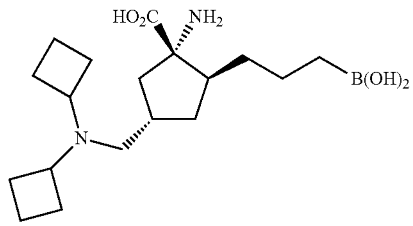 [SMILES: N[C@@]1(C(=O)O)C[C@@H](CN(C2CCC2)C2CCC2)C[C@@H]1CCCB(O)O] | (1S,2S,4S)-1-amino-2-(3-boronopropyl)-4-((dicyclobutylamino)methyl)cyclopentanecarboxylic acid |
| 7 | 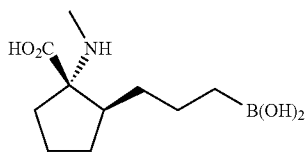 [SMILES: CN[C@@]1(C(=O)O)CCC[C@@H]1CCCB(O)O] | (1S,2S)-2-(3-boronopropyl)-1-(methylamino)cyclopentanecarboxylic acid |
| 8 | 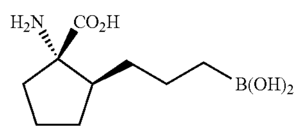 [SMILES: N[C@@]1(C(=O)O)CCC[C@@H]1CCCB(O)O] | (1S,2S)-1-amino-2-(3-boronopropyl)cyclopentanecarboxylic acid |
| 9 | 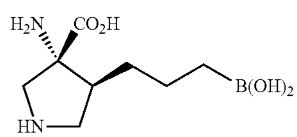 [SMILES: N[C@@]1(C(=O)O)CNC[C@@H]1CCCB(O)O] | (3R,4S)-3-amino-4-(3-boronopropyl)pyrrolidine-3-carboxylic acid |

Pharmaceutical Compositions and Dosages

The present invention is directed in part to pharmaceutical formulations of the inventive compounds and the use of the inventive formulations to treat disease conditions associated with an imbalance of arginase activity or the improper function of the arginase enzymes. Accordingly, in one embodiment the invention provides a pharmaceutical composition comprising a compound selected from Table 2 or a salt, solvate, stereoisomer, tautomer or prodrug thereof, and a pharmaceutically acceptable carrier.

TABLE 2

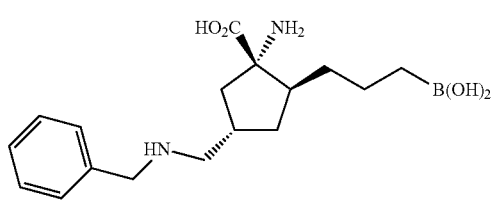 [SMILES: N[C@@]1(C(=O)O)C[C@@H](CNCc2ccccc2)C[C@@H]1CCCB(O)O]

TABLE 2-continued

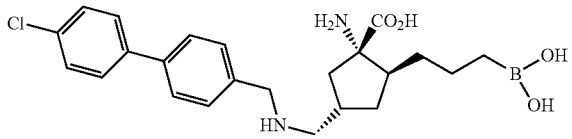

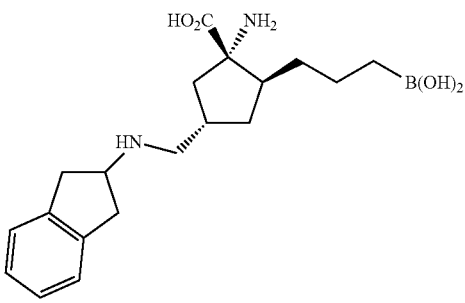 [SMILES: N[C@@]1(C(=O)O)C[C@@H](CNC2Cc3ccccc3C2)C[C@@H]1CCCB(O)O]

TABLE 2-continued

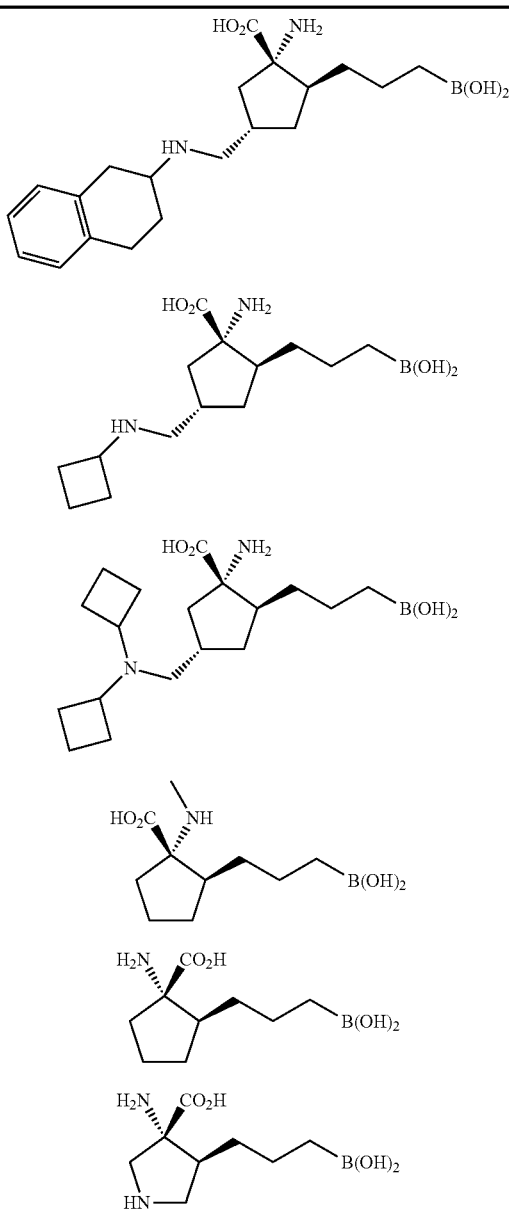

In one aspect, the present invention provides combination therapy in which a patient or subject in need of therapy is administered a formulation of the inventive compound in combination with one or more other compounds having similar or different biological activities.

According to one aspect of the combination therapy routine, a therapeutically effective dose of the inventive compound may be administered separately to a patient or subject in need thereof from a therapeutically effective dose of the combination drug. The person of skill in the art will recognize that the two doses may be administered within hours or days of each other or the two doses may be administered together.

Exemplary disease conditions for which combination therapy in accordance with the present invention may be administered include any of the conditions more specifically described hereinbelow. These include without limitation heart disease, hypertension, sexual disorders, gastric disorders, autoimmune disorders, parasitic infections, pulmonary disorders, smooth muscle relaxation disorders, asthma and hemolytic disorders.

Suitable compounds that may be used in combination with a compound according to the present invention include without limitation:

Erectile Dysfunction: sildenafil, vardenafil, tadalafil and alprostadil.

Pulmonary Hypertension/Hypertension: epoprostenol, iloprost, bosentan, amlodipine, diltiazem, nifedipine, ambrisentan and warfarin.

Asthma: fluticasone, budesonide, mometasone, flunisolide, beclomethasone, montelukast, zafirlukast, zileuton, salmeterol, formoterol, theophylline, albuterol, levalbuterol, pirbuterol, ipratropium, prednisone, methylprednisolone, omalizumab, corticosteroid and cromolyn.

Artherosclerosis: atorvastatin, lovastatin, simvastatin, pravastatin, fluvastatin, rosuvastatin, gemfibrozil, fenofibrate, nicotinic acid, clopidogrel.

The present invention also provides a pharmaceutically suitable composition comprising a therapeutically effective amount of one or more compounds of this invention or a pharmaceutically acceptable salt, solvate, stereoisomer, tautomer, or prodrug, in admixture with a pharmaceutically acceptable carrier. In some embodiments, the composition further contains, in accordance with accepted practices of pharmaceutical compounding, one or more additional therapeutic agents, pharmaceutically acceptable excipients, diluents, adjuvants, stabilizers, emulsifiers, preservatives, colorants, buffers, flavor imparting agents.

The inventive compositions can be administered orally, topically, parenterally, by inhalation or spray or rectally in dosage unit formulations. The term parenteral as used herein includes subcutaneous injections, intravenous, intramuscular, intrasternal injection or infusion techniques.

Suitable oral compositions in accordance with the invention include without limitation tablets, troches, lozenges, aqueous or oily suspensions, dispersible powders or granules, emulsion, hard or soft capsules, syrups or elixirs.

Encompassed within the scope of the invention are pharmaceutical compositions suitable for single unit dosages that comprise a compound of the invention its pharmaceutically acceptable stereoisomer, prodrug, salt, solvate, hydrate, or tautomer and a pharmaceutically acceptable carrier.

Inventive compositions suitable for oral use may be prepared according to any method known to the art for the manufacture of pharmaceutical compositions. For instance, liquid formulations of the inventive compounds contain one or more agents selected from the group consisting of sweetening agents, flavoring agents, coloring agents and preserving agents in order to provide pharmaceutically elegant and palatable preparations of the arginase inhibitor.

For tablet compositions, the active ingredient in admixture with non-toxic pharmaceutically acceptable excipients is used for the manufacture of tablets. Exemplary of such excipients include without limitation inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known coating techniques to delay disintegration and absorption in the gastrointestinal tract and thereby to provide a sustained therapeutic action over a desired time period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

For aqueous suspensions the inventive compound is admixed with excipients suitable for maintaining a stable suspension. Examples of such excipients include without limitation are sodium carboxymethylcellulose, methylcellulose, hydropylmethylcellulose, sodium alginate, polyvinylpyrrolidone, gum tragacanth and gum acacia.

Oral suspensions can also contain dispersing or wetting agents, such as naturally-occurring phosphatide, for example, lecithin, or condensaturatedion products of an alkylene oxide with fatty acids, for example polyoxyethylene stearate, or condensaturatedion products of ethylene oxide with long chain aliphatic alcohols, for example, heptadecaethyleneoxycetanol, or condensaturatedion products of ethylene oxide with partial esters derived from fatty acids and a hexitol such as polyoxyethylene sorbitol monooleate, or condensaturatedion products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents such as those set forth above, and flavoring agents may be added to provide palatable oral preparations. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

Pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensaturatedion products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative, and flavoring and coloring agents. The pharmaceutical compositions may be in the form of a sterile injectable, an aqueous suspension or an oleaginous suspension.

This suspension may be formulated according to the known art using those suitable dispersing or wetting agents and suspending agents which have been mentioned above. The sterile injectable preparation may also be sterile injectable solution or suspension in a non-toxic parentally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Compositions for parenteral administrations are administered in a sterile medium. Depending on the vehicle used and concentration the concentration of the drug in the formulation, the parenteral formulation can either be a suspension or a solution containing dissolved drug. Adjuvants such as local anesthetics, preservatives and buffering agents can also be added to parenteral compositions.

Synthesis of Compounds

In general, intermediates and target compounds containing chiral centers are designated stereospecifically. This designation is used primarily to distinguish relative stereochemistry and does not indicate optical purity. It will be obvious to those skilled in organic synthesis which compounds are optically pure by the methods used to prepare the compounds.

In addition, the compounds described below may also be isolated as hydrates or salts (e.g. hydrochloric acid salts) but are not necessarily designated as such. The compounds described in this invention are generally named using common names, IUPAC names, or names generated using the naming algorithm in ChemDraw 10.0.

Example 1

Preparation of (1S,2S,4S)-1-amino-2-(3-boronopropyl)-4-(((2,3-dihydro-1H-inden-2-yl)amino) methyl) cyclopentanecarboxylic acid

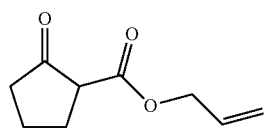

Step 1: Method A: allyl 2-oxocyclopentanecarboxylate (transesterification)

To a stirred solution of methyl 2-oxocyclopentanecarboxylate (4.26 g, 30 mmol) and allyl alcohol (10.2 mL, 150 mmol) in anhydrous toluene (25 mL) was added powdered zinc (0.40 g, 6 mmol). After refluxing the mixture for 48 h, it was cooled to room temperature and the suspension was filtered. The filter cake was rinsed with toluene and the combined filtrate was concentrated to afford allyl 2-oxocyclopentanecarboxylate (5.01 g, 99%) as a colorless oil. $^1$H NMR (CDCl$_3$, 300 MHz) δ 5.89 (ddt, $J_1$=15.9 Hz, $J_2$=10.5 Hz, $J_3$=4.8 Hz, 1 H), 5.33 (dtd, $J_1$=15.9 Hz, $J_2$=2.7 Hz, $J_3$=1.4 Hz, 1 H), 5.23 (dtd, $J_1$=10.5 Hz, $J_2$=2.7 Hz, $J_3$=1.4 Hz, 1 H), 4.83-4.75 (m, 1 H), 3.18 (t, J=9.0 Hz, 1 H), 2.41-2.23 (m, 4 H), 2.22-2.07 (m, 1 H), 1.94-1.80 (m, 1 H); MS (+CI): m/z for C$_9$H$_{12}$O$_3$: expected 168.1; found 169.1 (M+H)$^+$.

Step 1: Method B: allyl 2-oxocyclopentanecarboxylate (Dieckman)

To a stirring solution of diallyl adipate (4.53 g, 20 mmol) in anhydrous tetrahydrofuran (100 mL) at 0° C. was added lithium bis(trimethylsilyl)amide (40 mL, 1.0 N in THF, 40 mmol). After the addition was complete, the solution was warmed to room temperature and stirred for 2 hours. The reaction mixture was again cooled to 0° C. and the acidified by introducing acetic acid (2.53 mL, 44 mmol) in a dropwise manner. The addition of acetic acid resulted in a turbid mixture which mixture was warmed to room temperature and filtered. The filtrate obtained was concentrated, dissolved in minimal amount of dichloromethane and purified by flash column chromatography (silica gel, dichloromethane) to afford allyl 2-oxocyclopentanecarboxylate (2.62 g, 78%) as a colorless oil. The NMR spectrum for the purified product was the same as that observed for allyl 2-oxocyclopentanecarboxylate prepared using method A.

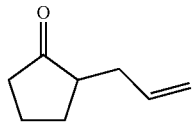

Step 2: Synthesis of 2-allylcyclopentanone

A stirring solution of palladium(II) acetate (51 mg, 0.23 mmol) and triphenylphosphine (0.24 g, 0.9 mmol) in anhydrous THF (20 mL) was heated under an atmosphere of nitrogen to 65° C. To the hot solution was added a solution of allyl 2-oxocyclopentanecarboxylate (2.52 g, 15 mmol) in anhydrous THF. After stirring at 65° C. for 45 the reaction mixture is cooled and concentrated. The resulting residual yellow oil was dissolved in a minimum amount of dichloromethane and purified by flash column chromatography (silica gel, dichloromethane) to afford 2-allylcyclopentanone (1.32 g, 71%) as a colorless oil. $^1$H NMR (CDCl$_3$, 300 MHz) δ 5.72 (ddt, $J_1$=17.1 Hz, $J_2$=10.2 Hz, $J_3$=7.2 Hz, 1 H), 5.09-4.98 (m, 2 H), 2.55-2.46 (m, 1 H), 2.35-2.22 (m, 1 H), 2.22-1.91 (m, 5 H), 1.87-1.70 (m, 1 H), 1.63-1.48 (m, 1 H).

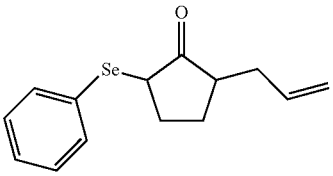 [SMILES: C=CCC1CCC([Se]c2ccccc2)C1=O]

Step 3: Synthesis of 2-phenylselenyl-5-(propene-3-yl)cyclopentanone, mixture of isomers A solution of 2-(propene-3-yl)cyclopentanone (12.4 g, 100 mmol) in anhydrous tetrahydrofuran (100 mL) was cooled to −70° C. under an inert atmosphere of nitrogen. To this cold solution was added 1 N lithium bis(tri-methylsilyl)amide in tetrahydrofuran (200 mL, 200 mmol) at a rate that effectively keeps the temperature of the reaction mixture below −55° C. Once the addition was complete, the mixture was stirred at −60 to −70° C. for one additional hour. A second solution of phenylselenyl chloride (19.5 g, 102 mmol) in anhydrous tetrahydrofuran (50 mL) was then added dropwise and stirring of the reaction mixture was continued at −60 to −70° C. for an additional 30 min. The reaction was then allowed to warm to 0° C. and quenched by the addition of a mixture of ethyl acetate (500 mL) and 5% aqueous citric acid (200 mL), while stirring the reaction mixture rapidly. After separation of the organic and aqueous layers, the aqueous solution was re-extracted with ethyl acetate (2×100 mL). The combined organic layers were washed with brine (200 mL), dried using (MgSO$_4$), and concentrated in vacuo. The residue was dissolved in heptane and chromatographed using a silica gel column (~600 ml) and a 2:1 heptane/methylene chloride solution as the starting eluent. The eluting solution was then changed to a 1:1 heptane/methylene chloride mixture to afford the subject compound (19.7 g, 71%) as a pale yellow oil. NMR (CDCl$_3$): δ 7.40-7.50 (m, 2 H), 7.05-7.25 (m, 3 H), 5.50-5.70 (m, 1 H), 4.80-4.95 (m, 2 H), 3.45-3.75 (m, 1 H), 2.30-2.50 (m, 1 H), 1.80-2.25 (m, 5 H), 1.50-1.75 (m, 1 H). MS (M+1): 279.1/280.9 (for 2 major isotopes of Se).

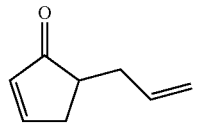

Step 4: Synthesis of 5-(propene-3-yl)cyclopent-2-enone

An ice cold (3° C.) solution of 2-phenylselenyl-5-(propene-3-yl)cyclopentanone, (mixture of isomers, (12.0 g, 43 mmol)) in methylene chloride (200 mL) was stirred in a 1 L round bottomed-flask that was equipped for boil-over containment. To this solution was added saturated aqueous ammonium chloride (45 mL), followed by dropwise addition of a 30% aqueous solution of hydrogen peroxide (22 mL). The reaction mixture was then slowly warmed to room temperature with intermittent cooling, as necessary, to prevent excess bubbling and boil-over. After stirring at room temperature for an additional hour the solution was washed with water (100 mL), followed by stirring with 10% aqueous sodium thiosulfate pentahydrate (75 mL) for 10 min, and the aqueous and organic layers were then allowed to separate. The organic solution was washed with saturated aqueous sodium bicarbonate and brine (75 mL each), dried using Na$_2$SO$_4$ and concentrated to a volume of about 30 mL. Purification of the crude reaction was effected by loading the crude mixture onto a silica gel column (~400 cc) using methylene chloride as the eluting solvent. Concentration of the appropriate fractions afforded 5-(propene-3-yl)cyclopent-2-enone (3.95 g, 75%) as a very pale yellow oil. NMR (CDCl$_3$): δ 7.61 (m, 1 H), 6.12 (m, 1 H), 5.60-5.75 (m, 1 H), 4.90-5.05 (m, 2 H), 2.70-2.80 (m, 1 H), 2.45-2.55 (m, 1 H), 2.30-2.40 (m, 1 H), 2.05-2.15 (m, 1 H).

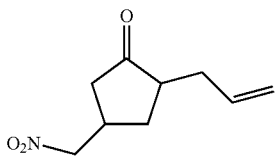

Step 5: Synthesis of 3-nitromethyl-5-(propene-3-yl)cyclopentanone, mixture of isomers A stirred solution of 5-(propene-3-yl)cyclopent-2-enone (0.428, 3.5 mmol) in nitromethane (2 mL) under nitrogen was treated with DOWEX® 550A-OH resin (0.80 g, which previously had been rinsed with methanol and partially air dried), and heated to 60° C. for 2 h. The mixture was cooled to room temperature, diluted with methylene chloride (20 mL), and filtered. The filtrate was concentrated in vacuo, redissolved in minimum methylene chloride, and loaded onto a silica gel column (~100 mL). Elution with methylene chloride afforded the subject compound (0.368 g, 57%) as a colorless oil. NMR (CDCl$_3$): δ 5.65-5.80 (m, 1 H), 5.00-5.15 (m, 2 H), 4.40-4.50 (m, 2 H), 2.85-3.15 (m, 1 H), 2.30-2.70 (m, 4 H), 1.90-2.20 (m, 3 H). MS (M+1): 183.9.

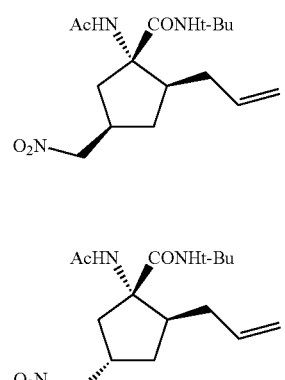

Step 6: Synthesis of 1-Acetamino-3-nitromethyl-5-(propene-3-yl)cyclopentanecarboxylic acid, t-butylamide, (isomers A and B)

To a stirring 2,2,2-trifluoroethanol (1.5 mL) solution of 3-nitromethyl-5-(propene-3-yl)cyclopentanone (mixture of isomers (0.366 g, 2.0 mmol)), under an inert atmosphere of nitrogen was added ammonium acetate (0.617 g, 8 mmol) and t-butylisonitrile (0.68 mL, 6.0 mmol) and the reaction mixture was stirred at room temperature for 2 days. The mixture was then diluted with methylene chloride (20 mL) and directly loaded onto a silica gel column (~250 mL). The two cyclopentane-t-butyl carboxamide isomers with the acetamino and allyl substituents in syn conformation (isomers 1 and 2), elute first, followed by elution of isomer A (122 mg, 19%), and then isomer B (195 mg, 30%) as white solids.

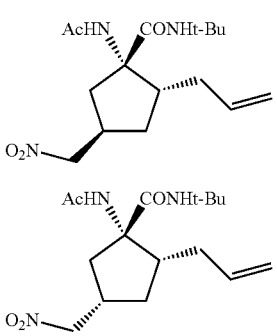

For isomer A: NMR (CDCl$_3$): δ 6.12 (br s, 2 H), 5.65-5.80 (m, 1 H), 5.00-5.15 (m, 2 H), 4.53 (d, J=7 Hz, 1 H), 4.35-4.50 (m, 1 H), 2.80-3.00 (m, 1 H), 2.45-2.60 (m, 1 H), 2.25-2.35 (m, 2 H), 1.90-2.20 (m, 2 H), 2.00 (s, 3H), 1.20-1.60 (m, 2 H), 1.34 (s, 9 H). MS (M+1): 326.0.

For isomer B: NMR (CDCl$_3$): δ 6.05-6.15 (m, 2 H), 5.65-5.80 (m, 1 H), 5.00-5.15 (m, 2 H), 4.43 (d, J=6.5 Hz, 2 H), 2.90-3.10 (m, 2 H), 2.40-2.50 (m, 1 H), 2.20-2.30 (m, 1 H), 2.00 (s, 3H), 1.70-2.00 (m, 4H), 1.35 (s, 9 H). MS (M+1): 326.0.

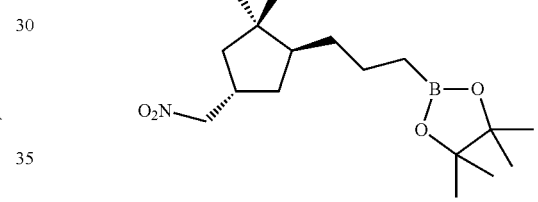

Step 7: Synthesis of (1S,2S,4S)-1-acetamido-N-(tert-butyl)-4-(nitromethyl)-2-(3-(4,4,5,5-tetramethyl-1,3,2-dioxaborolan-2-yl)propyl)cyclopentanecarboxamide To a stirred solution of 1-acetamino-3-nitromethyl-5-(propene-3-yl)cyclopentanecarboxylic acid, t-butylamide, isomer B (0.179 g, 0.55 mmol), in anhydrous methylene chloride (5 mL) under nitrogen was added chloro-1,5-cyclooctadiene iridium dimer (12 mg, 0.018 mmol) and Diphos® (14 mg, 0.035 mmol). After stirring for 30 minutes the reaction mixture was cooled to −25° C. Pinacolborane (0.123 mL, 0.85 mmol) was then added dropwise via syringe, and the reaction mixture was gradually allowed to warm to 0° C. (ice bath temperature) and then gradually was allowed to warm to room temperature overnight (18 h). The reaction was quenched by the addition of water (3 mL), stirred for 20 min at room temperature and then extracted twice with ethyl acetate (25 mL, and 10 mL respectively). The combined organic layers were washed with water then brine (20 mL each) and dried using MgSO$_4$. After concentration in vacuo the crude product was recrystallized from acetonitrile (2 crops) to afforded 0.173 g (69%) of the subject compound as a white solid. NMR (CDCl$_3$): δ 6.11 (br s, 1 H), 5.94 (br s, 1 H), 4.41 (d, J=7 Hz, 2 H), 3.00-3.15 (m, 1 H), 2.93 (dd, J=14 Hz, 9.5 Hz, 1H), 2.25-2.35 (m, 1 H), 2.00 (s, 3 H), 1.65-1.85 (m, 3 H), 1.15-1.50 (m, 4 H), 1.34 (s, 9 H), 1.24 (s, 12 H), 0.65-0.85 (m, 2 H). MS (M+1): 453.7.

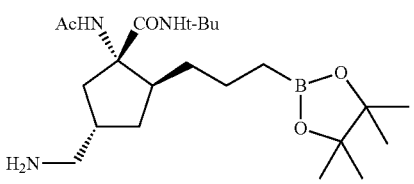

Step 8: Synthesis of (1S,2S,4S)-1-acetamido-4-(aminomethyl)-N-(tert-butyl)-2-(3-(4,4,5,5-tetramethyl-1,3,2-dioxaborolan-2-yl)propyl)cyclopentanecarboxamide To a stirring solution of (1S,2S,4S)-1-acetamido-N-(tert-butyl)-4-(nitromethyl)-2-(3-(4,4,5,5-tetramethyl-1,3,2-dioxaborolan-2-yl)propyl)cyclopentanecarboxamide (0.907 g, 2.0 mmol) in a mixture of tetrahydrofuran (20 mL), ethyl acetate (15 mL), and ethanol (5 mL) under nitrogen was added Raney nickel (1.2 g). The reaction mixture was then purged with hydrogen and stirred under an atmosphere of hydrogen at room temperature for 6 h. At the end of this period, the mixture was purged with nitrogen, then carefully through Celite®. After rinsing the filter cake with ethyl acetate the combined filtrate was concentrated in vacuo to afford the subject compound (0.841 g, 99%) as a white solid. NMR (CDCl$_3$): δ 6.98 (br s, 1 H), 6.93 (br s, 1 H), 2.55-2.70 (m, 3 H), 2.44 (m, 1 H), 2.24 (m, 1 H), 1.91 (m, 3 H), 1.50-1.65 (m, 3 H), 1.20-1.45 (m, 4 H), 1.26 (s, 9 H), 1.66 (s, 12 H), 0.60-0.75 (m, 2 H). MS (M+1): 424.4.

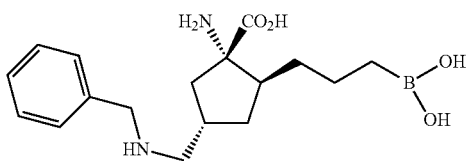 [SMILES: N[C@@]1(C(=O)O)C[C@@H](CNCc2ccccc2)C[C@@H]1CCCB(O)O]

Step 9: Synthesis of (1S,2S,4S)-1-amino-4-((benzylamino)methyl)-2-(3-boronopropyl)cyclopentanecarboxylic acid To a stirring solution of benzaldehyde (43 mg, 0.40 mmol) in methanol (3.5 mL) was added (1S,2S,4S)-1-acetamido-4-(aminomethyl)-N-(tert-butyl)-2-(3-(4,4,5,5-tetramethyl-1,3,2-dioxaborolan-2-yl)propyl)cyclopentanecarboxamide (148 mg, 0.35 mmol) and glacial acetic acid (one drop). The reaction mixture was stirred at 50° C. for 1 h, then cooled using an ice bath prior to adding sodium borohydride (17 mg, 0.45 mmol). After stirring for an additional hour (1 h) at 3° C., the reaction was allowed to warm to room temperature, and stirred for another 20 minutes. Following quenching of the reaction with water (1 mL)., the crude product mixture was treated with a 2:1:1 mixture of concentrated HCl:glacial acetic acid:water (8 mL) in a pressure bottle, stirred for 2 h at 60° C., and then capped and stirred for an additional 18 h at 130° C. The reaction mixture was then cooled to room temperature prior to uncapping of the pressure bottle. The crude mixture was diluted with water (20 mL), extracted with methylene chloride (20 mL) and concentrated in vacuo. The residue obtained was treated with water (20 mL) and concentrated three times to remove excess HCl. The crude reaction mixture was then dissolved in water (40 mL) and treated with DOWEX® 550A-OH resin (3 g) which had been rinsed with methanol prior to use. After stirring for 40 min, the reaction mixture was filtered and the resin washed successively with water, methanol and methylene chloride twice. Following washing, the resin was stirred with 1N HCl (15 mL×4) and filtered. The combined filtrates were concentrated and the residue was treated with water (20 mL) followed by concentration of the aqueous mixture three times to remove excess HCl. Purification of the crude product by HPLC followed by formation of the hydrochloride salt afforded the subject compound (71.4 mg, 50%) as a hygroscopic white foam. NMR (D$_2$O) δ 7.40 (br s, 5 H), 4.17 (br s, 2 H), 3.02 (d, J=5.5 Hz, 2 H), 2.70 (m, 1 H), 2.51 (m, 1 H), 2.15 (m, 1 H), 1.80 (m, 2 H), 1.55 (m, 1 H), 1.30-1.45 (m, 2 H), 1.20 (m, 1 H), 1.05 (m, 1 H), 0.60-0.75 (m, 2 H). MS (M+1): 335.5; MS (M−H$_2$O+1): 317.4; MS (M−2H$_2$O+1): 299.3.

Example 2

Preparation of (1S,2S,4S)-1-amino-2-(3-boronopropyl)-4-((((4'-chloro-[1,1'-biphenyl]-4-yl)methyl)amino)methyl)cyclopentanecarboxylic acid

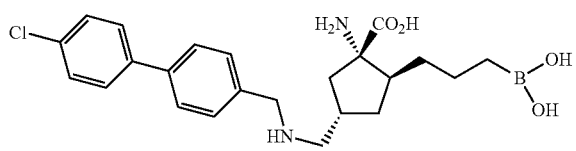 [SMILES: N[C@@]1(C(=O)O)C[C@@H](CNCc2ccc(-c3ccc(Cl)cc3)cc2)C[C@@H]1CCCB(O)O]

(1S,2S,4S)-1-amino-2-(3-boronopropyl)-4-((((4'-chloro-[1,1'-biphenyl]-4-yl)methyl)amino)methyl)cyclopentanecarboxylic acid was prepared in a manner analogous to that set fourth in Example 1, except 4'-chloro-[1,1'-biphenyl]-4-carbaldehyde was used as the aldehyde in step 9. NMR (D$_2$O) δ 7.65 (d, J=6 Hz, 2 H), 7.56 (d, J=6 Hz, 2 H), 7.47 (d, J =6 Hz, 2 H), 7.41 (d, J=6 Hz, 2 H), 4.20 (m, 2 H), 3.03 (m, 2 H), 2.70 (m, 1 H), 2.51 (m, 1 H), 2.10 (m, 1 H), 1.75 (m, 2 H), 1.52 (m, 1 H), 1.25-1.45 (m, 2 H), 1.16 (m, 1 H), 1.04 (m, 1 H), 0.55-0.70 (m, 2 H). MS (M+1): 445.3; MS (M−H$_2$O+1): 427.6; MS (M−2H$_2$O+1): 409.4.

Example 3

Preparation of (1S,2S,4S)-1-amino-2-(3-boronopropyl)-4-(((2,3-dihydro-1H-inden-2-yl)amino)methyl)cyclopentanecarboxylic acid

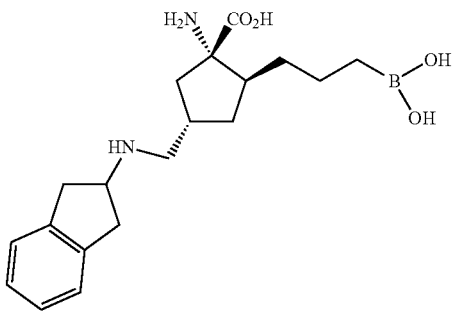 [SMILES: N[C@@]1(C(=O)O)C[C@@H](CNC2Cc3ccccc3C2)C[C@@H]1CCCB(O)O]

(1S,2S,4S)-1-amino-2-(3-boronopropyl)-4-(((2,3-dihydro-1H-inden-2-yl)amino)methyl)cyclopentanecarboxylic acid was prepared in a manner analogous to that set fourth in Example 1, except 1H-inden-2(3H)-one was used as the ketone in step 9. NMR (D₂O) δ 7.15-7.25 (m, 4 H), 3.46 (m, 1 H), 3.35 (dd, J=12.5 Hz, 5.5 Hz, 2 H), 3.00-3.15 (m, 4 H), 2.72 (m, 1 H), 2.55 (m, 1 H), 2.20 (m, 1 H), 1.85 (m, 2 H), 1.60 (m, 1 H), 1.35-1.50 (m, 2 H), 1.25 (s, 1 H), 1.05-1.15 (m, 1H), 0.60-0.75 (m, 2 H). MS (M+1): 361.3; MS (M−H₂O+1): 343.3; MS (M−2H₂O+1): 325.4.

Example 4

Preparation of (1S,2S,4S)-1-amino-2-(3-boronopropyl)-4-(((1,2,3,4-tetrahydronaphthalen-2-yl)amino)methyl)cyclopentanecarboxylic acid

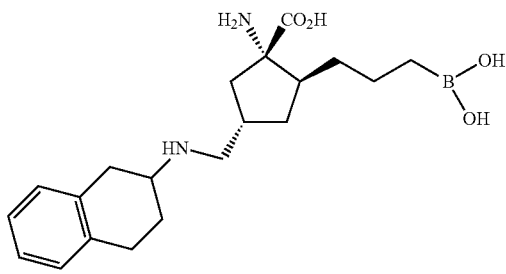 [SMILES: N[C@@]1(C(=O)O)C[C@@H](CNC2CCc3ccccc3C2)C[C@@H]1CCCB(O)O]

(1S,2S,4S)-1-amino-2-(3-boronopropyl)-4-(((1,2,3,4-tetrahydronaphthalen-2-yl)amino)methyl)cyclopentanecarboxylic acid was prepared in a manner analogous to that set fourth in Example 1, except 3,4-dihydronaphthalen-2(1H)-one was used as the ketone in step 9. NMR (D₂O) δ 7.05-7.15 (m, 4 H), 3.50 (m, 1 H), 3.21 (m, 1 H), 3.15 (d, J=5.5 Hz, 2H), 2.80-2.95 (m, 3 H), 2.73 (m, 1 H), 2.55 (m, 1 H), 2.20 (m, 2 H), 1.85 (m, 2 H), 1.75 (m, 1 H), 1.58 (m, 1 H), 1.30-1.50 (m, 2 H), 1.25 (s, 1 H), 1.10 (m, 1 H), 0.60-0.75 (m, 2 H). MS (M+1): 375.6; MS (M−H₂O+1): 357.5; MS (M−2H₂O+1): 339.4.

Example 5

Preparation of (1S,2S,4S)-1-amino-2-(3-boronopropyl)-4-((cyclobutylamino)methyl)cyclopentanecarboxylic acid

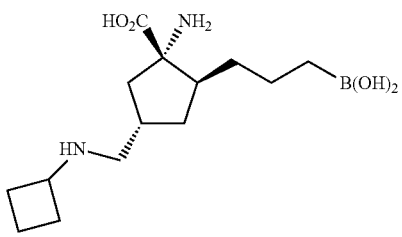 [SMILES: N[C@@]1(C(=O)O)C[C@@H](CNC2CCC2)C[C@@H]1CCCB(O)O]

(1S,2S,4S)-1-amino-2-(3-boronopropyl)-4-((cyclobutylamino)methyl) cyclopentanecarboxylic acid was prepared in a manner analogous to that set fourth in Example 1, except cyclobutanone was used as the ketone in step 9. Examples with one and two cyclobutane moieties incorporated were isolated from the same reaction. NMR (D₂O) δ 3.67 (m, 1 H), 2.89 (d, J=5.5 Hz, 2 H), 2.66 (m, 1 H), 2.50 (m, 1 H), 2.15-2.25 (m, 3 H), 2.00-2.10 (m, 2 H), 1.70-1.85 (m, 4 H), 1.53 (m, 1 H), 1.30-1.50 (m, 2 H), 1.23 (m, 1 H), 1.09 (m, 1 H), 0.60-0.75 (m, 2 H). MS (M+1): 299.6; MS (M−H₂O+1): 281.4; MS (M−2H₂O+1): 263.4.

Example 6

Preparation of (1S,2S,4S)-1-amino-2-(3-boronopropyl)-4-((dicyclobutylamino)methyl)cyclopentanecarboxylic acid

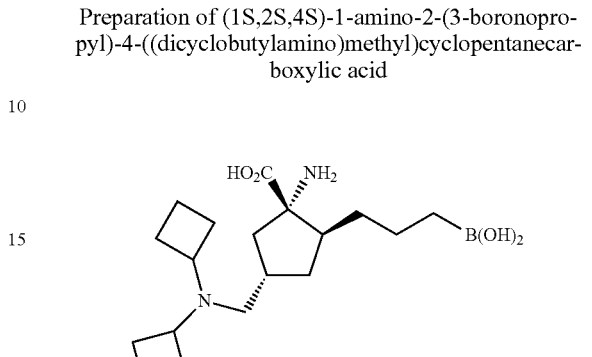

(1S,2S,4S)-1-amino-2-(3-boronopropyl)-4-((dicyclobutylamino)methyl) cyclopentanecarboxylic acid was prepared in a manner analogous to that set fourth in Example 1, except cyclobutanone was used as the ketone in step 9. Both mono cyclobutane and di-cyclobutane products were isolated from the same reaction. NMR δ 3.65-3.75 (m, 2 H), 2.90-3.05 (m, 2 H), 2.78 (m, 1 H), 2.54 (m, 1 H), 2.05-2.30 (m, 8 H), 1.60-1.90 (m, 6 H), 1.53 (m, 1 H), 1.44 (m, 2 H), 1.25 (m, 1 H), 0.85-1.15 (m, 2 H), 0.60-0.75 (2 H). MS (M+1): 353.5; MS (M−H₂O+1): 335.6; MS (M−2H₂O+1): 317.5.

Example 7

Preparation of (1S,2S)-2-(3-boronopropyl)-1-(methylamino) cyclopentanecarboxylic acid

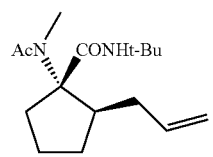

Step 1: Synthesis of (1S,2R)-2-allyl-N-(tert-butyl)-1-(N-methylacetamido) cyclopentanecarboxamide To a round bottom flask containing 2-(propene-3-yl)cyclopentanone (0.745 g, 6.0 mmol) was added a premixed slurry of 8 N methylamine/ethanol (3.0 mL, 24 mmol) and glacial acetic acid (1.37 mL, 24 mmol) in trifluoroethanol (3 mL). The reaction mixture is stirred for 30 minutes and then treated with t-butylisonitrile (2.04 mL, 18 mmol). After stirring for 2 days, the reaction mixture is diluted with methylene chloride (10 mL), and chromatographed using a silica gel column (175 mL). A gradient elution using 20%, 50%, and 80% mixture of ethyl acetate and heptane afforded the subject compound (559 mg, 33%) as a white crystalline solid. NMR (CDCl₃): δ 5.82 (br s, 1H), 5.70 (m, 1H), 4.90-5.00 (m, 2H), 2.96 (s, 3H), 2.63 (m, 1H), 2.37 (m, 1H), 2.26 (m, 1H), 2.04 (s, 3H), 1.60-1.85 (m, 4H), 1.40-1.60 (m, 2H), 1.24 (s, 9H). MS (M+1): 281.4; MS (M+Na): 303.4.

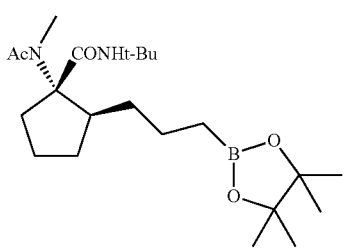

Step 2: Synthesis of (1S,2S)—N-(tert-butyl)-1-(N-methylacetamido)-2-(3-(4,4,5,5-tetramethyl-1,3,2-dioxaborolan-2-yl)propyl)cyclopentanecarboxamide To a solution of (1S,2R)-2-allyl-N-(tert-butyl)-1-(N-methylacetamido) cyclopentanecarboxamide (0.561 g, 2.00 mmol) in anhydrous methylene chloride (20 mL) maintained under an inert atmosphere of nitrogen was added chloro-1,5-cyclooctadiene iridium dimer (48 mg, 0.071 mmol) and 1,2-bis(diphenylphosphino)ethane (57 mg, 0.143 mmol). The reaction was stirred for 30 min, and then cooled to −25° C. Pinacolborane (0.44 mL, 3.0 mmol) was added dropwise to the cold mixture, and the mixture was slowly allowed to reach room temperature following addition of pinacolborane. After stirring at room temperature for 18 hours, water (12 mL) was added to the reaction mixture and the stirring was continued for an additional 30 minutes. The mixture was then extracted with ethyl acetate (75 mL, then 25 mL). The combined organic layer was washed with water then brine (50 mL each) and dried using MgSO$_4$ prior to concentration under vacuo. The residue obtained was dissolved in warm heptane and loaded onto a silica gel column (175 mL) that was initially eluted using a solvent mixture comprising 70% ethyl acetate/heptane, followed by ethyl acetate to afford the subject compound (0.611 g, 75%) as a white solid. NMR (CDCl$_3$): δ 5.64 (br s, 1 H), 2.94 (s, 3 H), 2.68 (m, 1 H), 2.22 (m, 1 H), 2.02 (s, 3 H), 1.85 (m, 1 H), 1.75 (m, 1 H), 1.35-1.60 (m, 5 H), 1.05-1.30 (m, 23 H), 0.65-0.80 (m, 2 H). MS (m+1): 409.5; MS (m+1): 431.5.

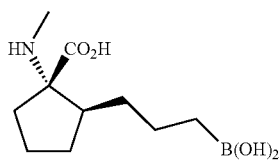 [SMILES: CN[C@@]1(C(=O)O)CCC[C@@H]1CCCB(O)O]

Step 3: Synthesis of (1S,2S)-2-(3-boronopropyl)-1-(methylamino) cyclopentanecarboxylic acid The solution of (1S,2S)—N-(tert-butyl)-1-(N-methylacetamido)-2-(3-(4,4,5,5-tetramethyl-1,3,2-dioxaborolan-2-yl)propyl)cyclopentanecarboxamide (0.600 g, 1.47 mmol) was hydrolyzed in a manner analogous to that described in Example 1, Step 9 to afford the subject compound (256 mg, 66%) as a pale amber glass. NMR (D$_2$O) δ 2.61 (s, 3 H), 2.30 (m, 1 H), 1.95-2.15 (m, 2 H), 1.80-1.95 (m, 2 H), 1.70 (m, 1 H), 1.35-1.50 (m, 3 H), 1.24 (m, 1 H), 1.00-1.15 (m, 1 H), 0.60-0.75 (m, 2 H). MS (M+1): 230.4; MS (M–H$_2$O+1): 212.2; MS (M–2H$_2$O+1): 194.2.

Example 8

Preparation of (1S,2S)-1-amino-2-(3-boronopropyl)cyclopentane carboxylic acid

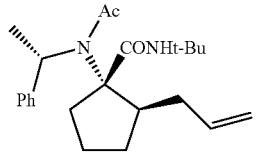

Step 1: Synthesis of (1S,2R)-2-allyl-N-(tert-butyl)-1-(N—((S)-1-phenylethyl)acetamido) cyclopentanecarboxamide To a stirring solution of 2-(propene-3-yl)cyclopentanone (0.745 g, 6.0 mmol) in 2,2,2-trifluoroethanol (5 mL) under an atmosphere of nitrogen was added (S)-α-methylbenzylamine (3.1 mL, 24 mmol), glacial acetic acid (1.38 mL, 24 mmol), and t-butylisonitrile (2.04 mL, 18 mmol). After stirring at room temperature for five days and then at 60° C. for an additional 2 days, the mixture was concentrated in vacuo, taken up in water (50 mL) and extracted using ethyl acetate (75 mL, then 50 mL). The combined organic layer was washed with brine (75 mL), dried using MgSO$_4$, and concentrated in vacuo. The residual oil was dissolved in minimum quantity of methylene chloride prior to loading of the crude onto a silica gel column (175 mL). The crude mixture was purified by eluting the column with 20% ethyl acetate/heptane and then using a solvent mixture comprising 30% ethyl acetate/heptane to afford the subject compound single enantiomer (0.341 g, 15%) as a pale yellow viscous oil. NMR (CDCl$_3$): δ 7.46 (m, 2 H), 7.31 (m, 2 H), 7.19 (m, 1 H), 6.27 (m, 1 H), 5.67 (m, 1 H), 4.90 (m, 2 H), 4.80 (br s, 1 H), 2.88 (m, 1 H), 2.43 (m, 2 H), 1.87 (m, 2 H), 1.50-1.80 (m, 10 H), 1.30 (s, 9 H). MS (M+1): 371.1; MS (M+Na): 393.4.

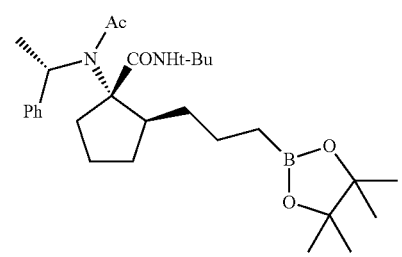

Step 2: Synthesis of (1S,2S)—N-(tert-butyl)-1-(N—((S)-1-phenylethyl)acetamido)-2-(3-(4,4,5,5-tetramethyl-1,3,2-dioxaborolan-2-yl)propyl)cyclopentanecarboxamide A solution of (1S,2R)-2-allyl-N-(tert-butyl)-1-(N—((S)-1-phenylethyl)acetamido) cyclopentanecarboxamide (0.322 g, 0.87 mmol) in anhydrous methylene chloride (8 mL), maintained under an inert atmosphere of nitrogen was treated with chloro-1,5-cyclooctadiene iridium dimer (20.5 mg, 0.030 mmol) and 1,2-bis(diphenylphosphino)ethane (24.3 mg, 0.060 mmol). After stirring for 30 minutes the reaction mixture was cooled to −30° C. Pinacolborane (0.19 mL, 1.3 mmol) was then added dropwise to the cold reaction mixture. Following the addition of pinacolborane the mixture was slowly allowed to warm to room temperature and stirred and stirred for an additional period of 18 h. Water (4 mL) was then added to the reaction and the mixture was stirred for an additional 30 minute. The crude product was extracted with ethyl acetate (30 mL, then 20 mL). The combined organic layer was washed with water, then brine (20 mL each), and dried using MgSO$_4$ prior to concentration in vacuo. The residue obtained was dissolved in a minimum quantity of methylene chloride and loaded onto a silica gel column (50 mL) that was eluted using 40% ethyl acetate/heptane to afford the target compound (285 mg, 66%) as a colorless viscous oil. NMR (CDCl$_3$): δ 7.47 (m, 2 H), 7.29 (m, 2 H), 7.15-7.22 (m, 1 H), 6.13 (br s, 1 H), 4.74 (br s, 1 H), 2.92 (m, 1 H), 2.30 (m, 1 H), 1.98 (m, 1 H), 1.40-1.80 (m, 11 H), 1.05-1.30 (m, 23H), 0.60-0.75 (m, 2 H). MS (m+1): 499.6; MS (m+1): 521.7.

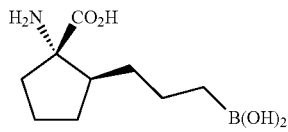

Step 3: Synthesis of (1S,2S)-1-amino-2-(3-borono-propyl)cyclopentanecarboxylic acid A cold (−50° C.) solution of (1S,2S)—N-(tert-butyl)-1-(N—((S)-1-phenylethyl) acetamido)-2-(3-(4,4,5,5-tetramethyl-1,3,2-dioxaborolan-2-yl)propyl)cyclopentane carboxamide (0.400 g, 0.802 mmol) in anhydrous tetrahydrofuran (5 mL) under an inert atmosphere of nitrogen was gradually combined (in small portions), with liquid ammonia (20 mL) and lithium wire (0.14 g, 20 mmol) over a time interval of several minutes. After stirring for 1.5 h at −40 to −50° C., the deep blue reaction was quenched with solid ammonium chloride, warmed slowly to room temperature, and residual ammonia driven off using nitrogen. Water (3 mL) was then added to the reaction flask and the mixture extracted with methylene chloride (3×30 mL). The combined organic layer was dried using Na$_2$SO$_4$ and concentrated in vacuo prior to purifification by HPLC to afford the subject compound (100 mg, 50%) as a white foam. NMR (D$_2$O) δ 2.32 (m, 1 H), 2.00 (m, 2 H), 1.77-1.90 (m, 2 H), 1.70 (m, 1 H), 1.35-1.50 (m, 3 H), 1.24 (m, 1 H), 1.12 (m, 1 H), 0.60-0.75 (m, 2 H). MS (M+1): 216.3; MS (M−H$_2$O+1): 198.2; MS (M−2H$_2$O+1): 180.3.

Example 9

Preparation of (3R,4S)-3-amino-4-(3-boronopropyl)pyrrolidine-3-carboxylic acid

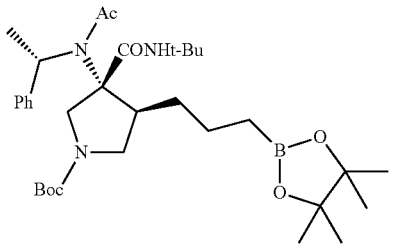

Step 1: Synthesis of (3R,4S)-tert-butyl 3-(tert-butyl-carbamoyl)-3-(N—((S)-1-phenylethyl)acetamido)-4-(3-(4,4,5,5-tetramethyl-1,3,2-dioxaborolan-2-yl)propyl) pyrrolidine-1-carboxylate To a stirring solution of (S)-tert-butyl 3-allyl-4-oxopyrrolidine-1-carboxylate (0.451 g, 2.0 mmol) in 2,2,2-trifluoroethanol (1.5 mL) under nitrogen was added (S)-α-methylbenzylamine (1.03 mL, 8 mmol), glacial acetic acid (0.46 mL, 8 mmol), and t-butylisonitrile (0.68 mL, 6 mmol). The reaction mixture was stirred at room temperature for three days and then at 60° C. for another 6 h. The mixture was then diluted with methylene chloride (15 mL) and added directly to a silica gel column (175 mL). Gardient elution of the column using 20%, 30%, and 40% ethyl acetate/heptane afforded a mixture of intermediate diastereomers (0.477 g, 51%, 2:1 mixture) which could not be resolved. To this mixture of diastereoisomers (0.472 g, 1.00 mmol) in anhydrous methylene chloride (5 mL) under an inert atmosphere of nitrogen was added chloro-1,5-cyclooctadiene iridium dimer (17 mg, 0.025 mmol) and 1,2-bis(diphenylphosphino)-ethane (20 mg, 0.05 mmol). The reaction mixture stirred for 30 min, and then cooled to −10° C. prior to the dropwise addition of pinacolborane (0.22 mL, 1.5 mmol). After adding pinacolborane the mixture was slowly allowed to reach room temperature and stirred at room temperature for 18 hours. Water (5 mL) was then added to the reaction flask and the mixture was stirred for an additional 30 minutes. The reaction mixture was then extracted with ethyl acetate (30 mL, then 15 mL). The combined organic solution was washed with water, then brine (20 mL each) and dried using MgSO$_4$ prior to concentration in vacuo. The residue obtained was dissolved in heptane containing a small amount of ethyl acetate and loaded onto a silica gel column (175 cc). Purification was effected by eluting the column with a mixture of ethyl acetate and heptane using the following concentrations—25% ethyl acetate/heptane, then 30% ethyl acetate/heptane, and finally 35% ethyl acetate/heptane to afford the subject compound (289 mg, 48%) as a colorless foam. NMR (CDCl$_3$): δ 7.70 (d, J=7.5 Hz, 2 H), 7.35 (t, J=7.5 Hz, 2 H), 7.25 (m, 1 H), 6.00 (m, 1 H), 4.88 (m, 1 H), 4.40-4.70 (m, 1 H), 3.80 (m, 1 H), 3.10-3.30 (m, 2 H), 2.70 (m, 1 H), 1.00-1.80 (m, 40 H), 0.60-0.80 (m, 2H). MS (M+1): 600.2.

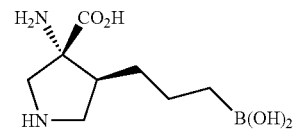 [SMILES: N[C@@]1(C(=O)O)CNC[C@@H]1CCCB(O)O]

Step 2: Synthesis of (3R,4S)-3-amino-4-(3-borono-propyl)pyrrolidine-3-carboxylic acid (S,S)-4-(N-Acetyl-N-(1S-phenethyl)amino)-4-(t-butylamino)carbonyl-3-(3-(4,4,5,5-tetramethyl-1,3,2-dioxaborolane-2-yl)propyl)pyrrolidine (0.165 g, 0.275 mmol) was purified by HPLC to afford the subject compound (61 mg, 77%) as a white solid. No additional procedure was required to remove the phenethyl group from amine. NMR (D$_2$O) δ 3.86 (d, J=12.5 Hz, 1 H), 3.70 (dd, J$_1$=11.5, J$_2$=8.5 Hz, 1 H), 3.42 (d, J=12.5 Hz, 1 H), 3.15-3.30 (m, 1 H), 2.45-2.60 (m, 1 H), 1.50-1.65 (m, 1 H), 1.10-1.40 (m, 3 H), 0.60-0.75 (m, 2 H). MS (M+1): 216.9; MS (M−H$_2$O+1): 199.0; MS (M−2H$_2$O+1): 180.9.

Routes of Administration and Dosing Regimen

Despite ample evidence associating arginase inhibition with therapies of various diseases and conditions, only a limited number of compounds are known that are capable of inhibiting arginase activity. The present invention therefore provides compounds and their pharmaceutical compositions that are useful in treating a subject suffering from such a disease or condition, as more generally set forth above.

The compounds of the invention can be formulated as described hereinabove and are suitable for administration in therapeutically effective amounts to the subject in any number of ways. The therapeutically effective amount of an inventive compound can depend upon the amounts and types of excipients used, the amounts and specific types of active ingredients in a dosage form, and the route by which the compound is to be administered to patients. However, typical dosage forms of the invention comprise a compound, or a pharmaceutically acceptable salt, solvate, hydrate, isomer, or prodrug thereof and a pharmaceutically acceptable carrier.

Typical dosage levels for a compound of the invention generally range from about 0.001 to about 100 mg per kg of the patient's body weight per day which can be administered in single or multiple doses. An exemplary dosage is about 0.01 to about 25 mg/kg per day or about 0.05 to about 10 mg/kg per day. In other embodiments, the dosage level is from about 0.01 to about 25 mg/kg per day, about 0.05 to about 10 mg/kg per day, or about 0.1 to about 5 mg/kg per day.

A dose typically ranges from about 0.1 mg to about 2000 mg per day, given as a single once-a-day dose or, alternatively, as divided doses throughout the day, optionally taken with food. In one embodiment, the daily dose is administered twice daily in equally divided doses. A daily dose range can be from about 5 mg to about 500 mg per day, such as, for example, between about 10 mg and about 300 mg per day. In managing the patient, the therapy can be initiated at a lower dose, perhaps from about 1 mg to about 25 mg, and increased if necessary from about 200 mg to about 2000 mg per day as either a single dose or divided doses, depending on the patient's global response.

Depending on the disease to be treated and the subject's condition, a pharmaceutically acceptable composition of the inventive compounds may be administered by oral, parenteral (e.g., intramuscular, intraperitoneal, intravenous, ICV, intracisternal injection or infusion, subcutaneous injection or implant), inhalation, nasal, vaginal, rectal, sublingual, or topical (e.g., transdermal, local) routes of administration. The compounds can be formulated, alone or together, in suitable dosage unit formulations containing conventional non-toxic pharmaceutically acceptable carriers, adjuvants and vehicles, as described above, that are appropriate for each route of administration. The invention also contemplates administration of the compounds of the invention in a depot formulation, in which the active ingredient is released over a defined time period.

Methods and Uses

The inventive compounds are useful for inhibiting the expression or activity of arginase I, arginase II or a combination of these enzymes. The enzymes of the arginase family play an important role in regulating the physiological levels of the L-arginine, a precursor of the signaling molecule nitric oxide (nitric oxide (NO)), as well as in regulating levels of L-ornithine, a precursor of certain polyamines that are important physiological signal transducers.

More specifically, the invention provides methods and uses for inhibiting arginase I, arginase II, or a combination thereof in a cell, comprising contacting the cell with at least one compound according to the present invention, or a composition thereof as described herein. In some embodiments, the invention provides a method for the treatment or prevention of a disease or condition associated with expression or activity of arginase I, arginase II, or a combination thereof in a subject.

For instance, the disease or condition is selected from the group consisting of cardiovascular disorders, gastrointestinal disorders, sexual disorders, pulmonary disorders, immune disorders, infection, autoimmune disorders, pulmonary disorders, and hemolytic disorders.

According to one embodiment, the inventive compounds are candidate therapeutics useful for treating cardiovascular disorders, such as diseases or conditions selected from the group consisting of hypertension, including, systemic hypertension, pulmonary arterial hypertension (PAH), pulmonary arterial hypertension in high altitude, ischemia reperfusion (IR) injury, myocardial infarction, atherosclerosis.

Exemplary sexual disorders that can be treated using the inventive compounds are disease or conditions selected from the group consisting of Peyronie's Disease and erectile dysfunction (ED).

In one embodiment an arginase inhibitor in accordance with the present invention is suitable for treating a pulmonary disorder selected from the group consisting of chemically-induced lung fibrosis, idiopathic pulmonary fibrosis, cystic fibrosis, chronic obstructive pulmonary disease (COPD and asthma.

Compounds in accordance with the present invention are also useful at treating gastrointestinal disorders, such as diseases or conditions selected from the group consisting of gastrointestinal motility disorders, gastric cancers, inflammatory bowel disease, Crohn's disease, ulcerative colitis, and gastric ulcers.

The transport of organs, such as liver, kidney and heart increases the risk of ischemic reperfusion injury (IR). The inventive compounds are useful in protecting transported organs from IR during transport.

According to an embodiment of the present invention, the inventive compounds are useful for treating autoimmune disorders. Exemplary diseases or conditions include without limitation encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

Arginase inhibitors in accordance with the present invention are also useful for treating immune disorders, such as a disease or condition selected from the group consisting of myeloid-derived suppressor cell (MDSC) mediated T-cell dysfunction, human immunodeficiency virus (HIV), autoimmune encephalomyelitis, and ABO mismatch transfusion reaction.

In one embodiment, the inventive compounds are useful as candidate therapeutics for treating a subject suffering from hemolytic disorders. Exemplary diseases or conditions include without limitation sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

Other exemplary disease conditions for which compounds described herein are candidate therapeutics are inflammation, psoriasis, leishmaniasis, neurodegenerative diseases, wound healing, hepatitis B virus (HBV), *H. pylori* infections, fibrotic diseases, arthritis, candidiasis, periodontal disease, keloids, adenotonsilar disease, African sleeping sickness, and Chagas' disease.

Advantageously, compounds in accordance with the present invention are especially useful at treating diseases or conditions selected from the group consisting of pulmonary arterial hypertension (PAH), erectile dysfunction (ED), hypertension, myocardial infarction, atherosclerosis, renal disease, asthma, inflammation, psoriasis, immune response, T-cell dysfunction, such as myeloid-derived suppressor cell (MDSC) mediated T-cell dysfunction, leishmaniasis, ischemia reperfusion injury, sickle cell disease, neurodegenerative diseases, wound healing, human immunodeficiency virus (HIV), hepatitis B virus (HBV), *H. pylori* infections, and fibrotic diseases such as cystic fibrosis. In addition, the compounds described herein are useful in the protection of organs, such as during organ transport.

In some embodiments, the subject receiving treatment is a mammal. For instance, the methods and uses described herein are suitable for medical use in humans. Alternatively, the methods and uses are also suitable in a veterinary context, wherein the subject includes but is not limited to a dog, cat, horse, cow, sheep, lamb and reptile.

More specific descriptions of diseases and conditions follow below.

Erectile Dysfunction

The observation that there are differences in the activity of arginase in the penis of young mice versus older mice led to the conclusion that arginase may play a role in erectile dysfunction (ED). In this context, Champion et. al., (Am. J. Physiol. Heart Circ. Physiol. 292:340-351, (2006) and Biochem. and Biophys. Research Communications, 283:923-27, (2001)), observed an increase of mRNA expression levels and arginase protein in aged mice along with a reduction in the activity of constitutively active NOS.

Nitric oxide is implicated in nonadrenergic, noncholinergic neurotransmission that leads to smooth-muscle relaxation in the corpus cavernosum enabling penile erection (New England Journal of Medicine, 326, (1992)), Hence, erectile dysfunction can often be treated by elevating penile tissue nitric oxide (NO) levels. Such an elevation in tissue nitric oxide (NO) levels can be achieved by inhibiting arginase activity in penile tissue of aged subjects. Stated differently, arginase has been postulated to deplete the pool of free L-arginine available to NOS in cells which results in lower levels of nitric oxide (NO) and erectile dysfunction. See, Christianson et. al., (Acc. Chem. Res., 38:191-201, (2005)), and (Nature Structural Biol., 6(11):1043-1047, (1999)) Inhibitors of arginase, therefore, can play a role in the treatment of erectile dysfunction.

Pulmonary Hypertension

It has been proposed that alterations in arginine metabolism are involved in the pathogenesis of pulmonary hypertension (Xu et al., FASEB J., 18:1746-48, 2004). The proposition is based in part on the finding that arginase II expression and arginase activity are significantly elevated in pulmonary artery endothelial cells derived from lung explants of patients with class I pulmonary hypertension.

Additionally, secondary pulmonary hypertension is emerging as one of the leading causes of mortality and morbidity in patients suffering from hemolytic anemias, such as thalassemia and sickle cell disease. The underlying cause for secondary pulmonary hypertension is impaired nitric oxide bioavailability due to release of arginase following hemolysis which decreases the pool of free arinine that is required for nitric oxide (NO) synthesis. Accordingly, inhibition of arginase activity can provide a potential therapeutic avenue for treating pulmonary hypertension.

Hypertension

Xu, W. et al., *FASEB* 2004, 14, 1746-8 proposed a fundamental role of arginase II in blood pressure regulation. In this context, high levels of vascular arginase are correlated to concomitant reduction of vascular nitric oxide (NO) in hypertensive animals. For instance, up-regulation of arginase activity precedes a rise in blood pressure in rats that were genetically predisposed to hypertension (i.e., spontaneously hypertensive rats), but administration of the anti-hypertensive agent hydralazine lowered blood pressure with a decrease in the expression levels of vascular arginase, thereby indicating a strong correlation between the arginase activity and blood pressure (Berthelot et al. Life Sciences, 80:1128-34, (2008). Similar administration of the known arginase inhibitor $N^{\omega}$-hydroxy-nor-L-arginine (nor-NOHA) lowered blood pressure and improved the vascular response of resistance vessels to blood flow and pressure in spontaneously hypertensive animals, thereby highlighting inhibitors of arginase as candidate therapeutics for treating hypertension (Demougeot et al., (J. Hypertension, 26:1110-18, (2008).

Arginase also plays a role in reflex cutaneous hypertension by lowering the cellular levels of nitric oxide (NO). Nitric oxide causes vasodilation and levels of nitric oxide (NO) are normally elevated or lowered to maintain blood pressure at physiologically acceptable levels. Kenny et al., (J. of Physiology 581 (2007) 863-872), hypothesized that reflex vasodilation in hypertensive subjects can attenuate arginase inhibition, thereby implicating a role for arginase inhibitors for the treatment of hypertension.

Asthma

Arginase activity is also associated with airway hyperresponsiveness in asthma. For example, arginase I is upregulated in human asthmatics and in mice suffering from acute and chronic asthma, whilst levels of arginase II and NOS isoforms remain unchanged (Scott et al., Am. J. Physiol. Lung Cell Mol. Physiol. 296:911-920 (2009)). Furthermore, methacholine induced responsiveness of the central airways in the murine chronic model attenuated upon the administration of the arginase inhibitor S-(2-boronoethyl)-L-cysteine. The similarity between expression profiles of ARG I in humans and in mice having chronic asthma indicates that compounds capable of inhibiting arginase activity are candidate therapeutics for treating asthma.

Other lines of evidence reveal further correlations between increased activity of arginase in asthmatic lung tissue and disease progression, such as an upregulation for genes related to the metabolism of cationic amino acids, including arginase I and II in mice having asthma (Rothenberg et al., (J. Clin. Invest., 111:1863-74 (2003), and Meurs et. al., (Expert Opin. Investig Drugs, 14 (10:12211231, (2005)).

Further, levels of all amino acids are lower in the plasma of asthmatics, but the levels of arginine are significantly lower in plasma compared to that of a normal subject (Morris et al., (Am. J. Respir. Crit Care Med., 170:148-154, (2004)). Thus, arginase activity is significantly increased in the plasma from an asthmatic, in which elevated levels of arginase activity may contribute to the lower bioavailability of plasma arginine that creates an nitric oxide (NO) deficiency, which is responsible for promoting hyperreactive airways in asthmatics.

Inflammation

Arginase activity also is associated with autoimmune inflammation (Chen et al., Immunology, 110:141-148, (2003)). The authors identified upregulation in the expression levels of the ARG I gene in murine spinal cells from animals undergoing experimental autoimmune encephalomyelitis (EAE). Administration of the arginase inhibitor amino-6-boronohexanoic acid (ABH), however, resulted in the animals developing a much milder form of EAE than in control animals. These results implicate inhibitors of arginase in a therapeutic role for treating autoimmune encephalomyelitis.

Moreover, Horowitz et al., (American J. Physiol Gastrointestinal Liver Physiol., 292:G1323-36, (2007)), suggest a role for arginase enzymes in vascular pathophysiology. For example, these authors indicate a loss of nitric oxide (NO) production in chronically inflamed gut blood vessels in patients suffering from irritable bowel disease (IBD), Crohn's disease and ulcerative colitis. The loss in nitric oxide (NO) production correlated with an upregulation of arginase expression and activity that reduced levels of arginine preventing nitric oxide synthase (NOS), from synthesizing nitric oxide (NO) Inhibitors of arginase activity, therefore, may be candidate therapeutics for treating vascular pathophysiology.

Ischaemia Reperfusion

Arginase inhibition is also suggested to play a cardioprotective role during ischaemia reperfusion. More specifically, inhibition of arginase protects against myocardial infarction by a mechanism that may be dependent on NOS activity and the consequent bioavailability of nitric oxide (NO) (Pernow et al., (Cardiovascular Research, 85:147-154 (2010)).

Myocardial Infarction and Artherosclerosis

Arginase I polymorphism is associated with myocardial infarction along with an increased risk of developing carotid artery intima media thickness that is considered to be a reliable indicator of arthrosclerosis as well as of other coronary arterial diseases (Brousseau et al., (J. Med Genetics, 44:526-531, (2007)). Increased arginase activity elevates levels of ornithine that is biochemically involved in promoting the formation of the matrix and cellular components of artherosclerotic plaque. Id. Thus, arginase inhibitors may serve as candidate therapeutics for treating artherosclerosis. Berkowitz et al., (Circ. Res. 102, 102, (2008), p. 923-932), implicated a role for ARGII in the formation of plaque and artherosclerosis. Oxidation of LDLP that accompanies plaque formation increases arginase activity and lower nitric oxide (NO) levels in endothelial cells. In particular, levels of ARGII are elevated in artherosclerotic mice, indicating a role for inhibitors of arginase as candidate therapeutics for treating artherosclerosis.

Additionally, studies by Ming et. al., (Current Hypertension Reports., 54:54-59, (2006)), indicate that an upregulation of arginase rather than endothelial nitric oxide (NO) dysfunction plays an important role in cardiovascular disorders, including artherosclerosis. That arginase is involved in cardiovascular diseases is further supported by the observation ARGI and ARGII activity is upregulated in cardiac myocytes which in turn negatively impacts NOS activity and myocardial contractility. (See, Margulies et. al., Am. J. Physiol. Heart Circ. Physiol., 290:1756-62, (2006)).

Immune Response

The arginine/nitric oxide (NO) pathway may also play a role in immune response, such as after organ transplants. For instance, it was postulated that reperfusion of an orthotopic liver transplant graft caused a significant increase in ornithine levels due to upregulation of arginase activity in the graft (Tsikas et al., (Nitric oxide, 20:61-67, (2009)). The elevated levels of hydrolytic and proteolytic enzymes in the graft may result in a less favorable outcome for the grafted organ. Thus, inhibiting the arginase enzymes may present an alternate therapeutic avenue for improving the outcome of a transplant.

Psoriasis

Arginase has been implicated to play a role in the pathogenesis of psoriasis. For example, ARG I is highly expressed in hyperproliferative psoriasis, and in fact, it is responsible for down regulation of nitric oxide (NO) an inhibitor of cell proliferation, by competing for the common substrate L-arginine as postulated by D. Bruch-Gerharz et al. *American Journal of Pathology* 162(1) (2003) 203-211. More recent work by Abeyakirthi et al. (British J. Dermatology, (2010)), and Berkowitz et al, (WO/2007/005620) support the finding of low nitric oxide (NO) levels in psoriatic keratinocytes. Abeyakirthi et al, found that psoriatic keratinocytes were poorly differentiated and hyperproliferative. The poor differentiation was postulated to result from low levels of nitric oxide (NO), not because of poor expression of NOS, but rather the over expression of arginase that competes with NOS for substrate L-arginine. Thus, inhibition of arginase may provide therapeutic relief from psoriasis.

Wound Healing

Under normal physiological conditions, nitric oxide (NO) plays an important role in promoting wound healing. For example, Hulst et al., (Nitric Oxide, 21:175-183, (2009)), studied the role of ARGI and ARG II in wound healing. Immediately following injury, it is desirable to elevate tissue levels of nitric oxide (NO) so as to promote angiogenesis and cell proliferation that are important for healing Inhibitors of arginase may therefore find use as therapeutics to treat wounds because such compounds would elevate tissue levels of nitric oxide (NO). Further support for the use of arginase inhibitors as candidate therapeutics for treating wounds was provided by South et al. (Experimental Dermatology, 29:664-668 (2004)), who found a 5-fold increase in arginase I in chronic wounds such as skin erosions and blisters.

Cystic Fibrosis

Cystic fibrosis (CF) is a multisystem disorder caused by mutations of the cystic fibrosis transmembrane conductance regulator (CFTR) gene. The common symptoms of CF are persistent pulmonary infection, difficulty in breathing, pancreatic insufficiency, and elevated sweat chloride levels. CF can be fatal if untreated, with pulmonary diseases, resulting from mucus build-up and decreased mucociliary clearance, being the leading cause of morbidity and mortality.

It has been asserted that patients with cystic fibrosis (CF) have increased plasma and sputum arginase activity, with an accompanying decrease in the levels of plasma l-arginine (H. Grasemann et al., *Am. J. Respir. Crit. Care Med.* 172(12) (2005) 1523-1528. The increased arginase activity, however, results in lower physiological levels of nitric oxide (NO) that can cause airway obstruction decreased pulmonary function in patients suffering from cystic fibrosis (CF).

Impaired electrical field induced-stimulation of smooth muscle relaxation in the airway of a mouse model of CF and the administration of l-arginine and NO reversed this effect as proposed by M. Mhanna et al. *Am. J. Respir. Cell Mol. Biol.* 24(5) (200)1 621-626. Graesmann et al., found a positive correlation exists between pulmonary function and exhaled NO and NO metabolite concentrations in the sputum of CF patients (Grasemann, H; Michler, E; Wallot, M; Ratjen, F., *Pediatr Pulmonol.* 1997, 24, 173-7).

Taken together, theses results indicate that increased Arginase activity in CF contributes to the NO deficiency and pulmonary obstruction in CF by limiting the availability of l-arginine to NOS. Thus, inhibitors of arginase activity are candidate therapeutics for treating cystic fibrosis (CF)

Organ Protection

Another therapeutic avenue for compounds in accordance with the present invention is protecting organs during transport from donor to a site where they will be transplanted into a recipient. Ischemic reperfusion injury (IR) due to exposure of the transplant organs to a period of warm ischemia (time from donor until flushed with preservation media), and cold ischemia (hypothermic preservation) is frequently observed in patients undergoing transplant surgery. Ischemic reperfusion injury (IR) and accompanying primary graft dysfunction and/or acute or chronic rejection results due to alteration in the cellular activity of the L-Arginine/NO pathway.

It was proposed that Arginase 1 and arginase 2 are released from apoptotic endothelial cells and kidney cells within the first 24 hours of organ removal from the body. To counteract the released arginase, L-Arginine is added to preservation media. Results with canine kidney transplants indicate that addition of L-arginine reduced the incidence and severity of ischemia, resulted in post-transplant with lower MDA levels at 1 hour, and lowered BUN & Serum creatinine levels during the first 72 hrs. See Erkasap, S; Ates, E., *Nephrol Dial Transplant*. 2000, 15, 1224-7.

Similar results were observed for canine lung grafts over a 24 hour period when lungs were preserved in the University of Wisconsin solution supplemented with L-Arginine. Yen et al., observed that the addition of L-arginine to the preservation medium increased pulmonary endothelial protection and lowered the incidence of ischemia when compared to a control that is preserved in medium that does not contain L-arginine (Chu, Y; Wu, Y. C.; Chou, Y. C.; Chueh, H. Y, Liu H P, Chu J J, Lin P J., *J Heart Lung Transplant*. 2004, 23, 592-8).

Koch et al. stated that improved myocardial contractility and relaxation in heart muscle of rats following transplantation when hearts were preserved in HTK solution having L-Arginine and N-alpha-acetyl-histidine (Koch A, Radovits T, Loganathan S, Sack F U, Karck M, Szabo G B., *Transplant Proc*. 2009, 41, 2592-4).

Addition of an arginase inhibitor, therefore, can be a candidate therapeutic for preventing and/or reducing the incidence and risk of ischemic reperfusion injury by a synergistically increasing the organ protective effect of the preservation media. Given the low number of available organs that are suitable for transplant and the loss and injury of organs due to the onset of ischemia, arginase inhibitors in accordance with the present invention can find use as therapeutics for preserving organs, increasing organ availability by reducing the amount of ischemic reperfusion injury during organ transport.

Leishmaniasis

Leishmaniasis is caused by a protozoan and manifests as cutaneous leishmaniasis (i.e., skin infection causing hypopigmented nodules) and visceral lieshmaniasis (more severe affecting internal organs). Arginase it postulated to play a role in disease progression since the parasite relies on arginase for the synthesis of cellular polyamines that are essential for pathogenesis Inhibition of arginase, therefore, would reduce cellular parasitic burden and promote increased nitric oxide (NO) levels enhancing parasitic clearance. See Liew F Y et al. *Eur J Immunol* 21 (1991) 2489, Iniesta V et al. *Parasite Immunol*. 24 (2002) 113-118, and Kane M M et al. *J. Immunol*. 166 (2001) 1141-1147. Compounds according to the present invention, therefore can be used as therapeutics for treating liesmaniasis.

Myeloid Derived Suppressor Cells (MDSC)

MDSC's are potent immune modulators that limit immune responses through several pathways, such as, L-arginine depletion via arginase 1 release into the microenvironment (Rodriguez 2009 Cancer Res), MHC restricted suppression (Nagaraj S, Gupta K, Pisarev V, Kinarsky L, Sherman S, Kang L, Herber D L, Schneck J, Gabrilovich D I., *Nat Med*. 2007, 13, 828-35), induction of T regulatory cells (Serafini P, Mgebroff S, Noonan K, Borrello I., *Cancer Res*. 2008, 68, 5439-49), and production of IL10 (Rodrigues J C, Gonzalez G C, Zhang L, Ibrahim G, Kelly J J, Gustafson M P, Lin Y, Dietz A B, Forsyth P A, Yong V W, Parney I F., *Neuro Oncol*. 2010, 12, 351-65) (Sinha P, Clements V K, Bunt S K, Albelda S M, Ostrand-Rosenberg S., *J Immunol*. 2007, 179, 977-83), for instance.

It is postulated that tumor development is accompanied by an increase in the number of MDSC's both peripherally and infiltrated within tumors. See Almand B, Clark J I, Nikitina E, van Beynen J, English N R, Knight S C, Carbone D P, Gabrilovich D I., *J Immunol*. 2001, 166, 678-89 and Gabrilovich D., *Nat Rev Immunol*. 2004, 4, 941-52. Treatment of tumor bearing mice with established chemotherapeutics such as gemcitabine and 5-Fluorouracil eliminates MDSC immunesuppression and results in delayed tumor growth. See Le H K, Graham L, Cha E, Morales J K, Manjili M H, Bear H D., *Int Immunopharmacol*. 2009, 9, 900-9 and Vincent J, Mignot G, Chalmin F, Ladoire S, Bruchard M, Chevriaux A, Martin F, Apetoh L, Rébé C, Ghiringhelli F., *Cancer Res*. 2010, 70, 3052-61, respectively. Moreover, inhibition of arginase 1 enhanced antitumor immunity by reducing MDSC function. Thus, inhibitors of arginase, such as compounds in accordance with the present invention reduce or delay tumor growth and can be used in combination with established anti-cancer agents in the treatment of cancer.

*Helicobacter pylori* (*H. pylori*)

*Helicobacter pylori* (*H. pylori*) is a Gram-negative bacterium that colonizes the human gastric mucosa. Bacterial colonization can lead to acute or chronic gastritis and is highly associated with peptic ulcer disease and stomach cancer. The observation that the addition of L-arginine to co-culture of *H. pylori* and macrophages increased nitric oxide (NO) mediated killing of the *H. pylori* (Chaturvedi R, Asim M, Lewis N D, Algood H M, Cover T L, Kim P Y, Wilson K T., *Infect Immun*. 2007, 75, 4305-15), supports the hypothesis that bacterial arginase competes with macrophage arginase for free arginine that is required for nitric oxide (NO) synthesis. See Gobert A P, McGee D J, Akhtar M, Mendz G L, Newton J C, Cheng Y, Mobley H L, Wilson K T., *Proc Natl Acad Sci USA*. 2001, 98, 13844-9. L-arginine is required for T-cell activation and for the rapid clearance of bacteria from infected cells. By depleting the pools of free L-arginine in vivo, *H. pylori* reduces arginine-induced CD3zeta expression on T-cells and prevents T-cell activation and proliferation. See Zabaleta J, McGee DJ, Zea AH, Hernandez C P, Rodriguez P C, Sierra R A, Correa P, Ochoa A C., *J Immunol*. 2004, 173, 586-93.

The inhibition of bacterial arginase using the known inhibitor NOHA, however, reestablished CD3 expression on T-cells and (Zabaleta J 2004), and enhanced production of NO by macrophages, thus, promoting macrophage mediated clearance of bacteria from infected cells. See Chaturvedi R, Asim M, Lewis N D, Algood H M, Cover T L, Kim P Y, Wilson K T., *Infect Immun*. 2007, 75, 4305-15.

Furthermore, Lewis et al., have suggested a role for arginase II in *H. pylori* infection. For example, these authors indicate that argII−/− primary macrophages incubated with *H. pylori* extracts showed enhanced NO production and correspondingly an increased (~15%) NO-mediated killing of bacterial cells (Lewis N D, Asim M, Barry D P, Singh K, de Sablet T, Boucher J L, Gobert A P, Chaturvedi R, Wilson K T., *J Immunol*. 2010, 184, 2572-82) Inhibitors of arginase activity, therefore, may be candidate therapeutics for treating vascular pathophysiology Inhibitors of arginase activity, therefore, may be candidate therapeutics for treating *H. pyrlori* infections and for treating gastric ulcers, peptic ulcers and cancer.

Sickle Cell Disease (SCD)

Sickle-cell disease (SCD), or sickle-cell anaemia, or drepanocytosis, is a genetic blood disorder, characterized by red blood cells that assume an abnormal, rigid, sickle shape. Sickling decreases the cells' flexibility and increases the risk of complications. An increase in the concentration of reactive oxygen species (ROS) in circulation causes adherence of blood cells and consumption of NO that results in poor vasodilation or the inability of blood vessels to vasodilate. The inability to vasodilate along with the increased adherence of blood cells in SCD results in vaso occlusive crisis and pain.

Low levels of plasma L-arginine are normally detected in patients with SCD (Morris C R, Kato G J, Poljakovic M, Wang X, Blackwelder W C, Sachdev V, Hazen S L, Vichinsky E P, Morris S M Jr, Gladwin M T., *JAMA.* 2005, 294, 81-90) According to these authors, lysis of red blood cells (RBC's) in patients suffering from SCD causes the release of arginase and a subsequent lowering of physiological L-Arginine levels. This sequence of biological events lowers physiological concentrations of nitric oxide (NO), a signaling molecule that plays a role in vasodilation. Other biological events also limit NO bioavailabilty. These include, for example, the uncoupling of nitric oxide synthase (NOS), and the subsequent decrease in physiological NO levels, as well as the reaction of superoxide ($O^{-2}$) reactive oxygen species with NO to sequester the latter as $ONOO^-$.

Based on theses observations, inhibitors of arginase, especially arginase I inhibitors are being proposed by the present inventors as candidate therapeutics for patients with sickle cell disease. As stated above, SCD causes the uncoupling of eNOS due to low physiological levels L-arginine Inhibition of arginase present in the blood circulation, however, may address this problem by increasing the physiological levels L-arginine, the substrate of endothelial nitric oxide synthase (eNOS). This sequence of events, importantly, are proposed by the present inventors to enhance endothelial function and relieve vasoconstriction associated with SCD.

Human Immunodeficiency Virus (HIV)

HIV is caused by virus that infects CD4+ helper T cells and causes severe lymphopaenia that predisposes the infected individuals to opportunistic infection. Although, anti-retroviral therapy (ART) is extensively used to combat HIV infection, the wide spread use of anti-retroviral drugs has resulted in the generation of resistant strains of HIV.

A correlation exists between the activity of arginase in patients suffering from HIV and the severity of HIV disease. That is increased arginase activity has been correlated to increased viral titres in HIV patients. These patients also show decrease serum arginine levels as well as decreased levels of CD4+/CD8+ cells.

Taken together, these observations suggest a role for arginase inhibitors, such as compounds according to Formulae I or II as candidate therapeutics in the treatment of HIV infection.

Chronic Hepatitis B Virus (HBV)

Chronic hepatitis B infection is a viral disease that is transmitted by contact with infected body fluids. Chronic HBV infections are characterized by inflammation of the liver and jaundice and if left untreated can cause cirrhosis of the liver that can progresses to form hepatocellular carcinomas. Antiviral drugs currently used, however, have low efficacy against chronic HBV infections. Serum and liver homogenates of patients with chronic HBV infections show reduced levels of arginine and increased arginase activity. For infected patients moreover, the increased arginase activity is correlated to an impaired cytotoxic T-lymphocytes (CTL) response with reduced IL-2 production and CD3z expression.

Replenishing serum arginine to physiologically acceptable levels, however, reconstituted CD3z and IL-2 expression, implicating a role for arginase inhibitors as potential therapeutics in the treatment of chronic HBV infections.

Inhibition of Arginase

The inventive compounds inhibit human arginase I (ARG I) and arginase II (ARG II) as evidenced by an ex vivo assay set forth by a published protocol (Baggio et al. *J. Pharmacol. Exp. Ther.* 1999, 290, 1409-1416). The assay established the concentration of inhibitor that is required to reduce arginase activity by 50% ($IC_{50}$).

Assay Protocol

Inhibition of arginase I (ARG I) and arginase II (ARG II) by the inventive compounds is followed spectrophotometrically at 530 nm. The compound to be tested is dissolved in DMSO at an initial concentration 50-fold greater than its final concentration in the cuvette. 10 µl of the stock solution is diluted in 90 µl of the assay buffer that comprises 0.1M sodium phosphate buffer containing 130 mM NaCl, pH 7.4, to which is added ovalbumin (OVA) at a concentration of 1 mg/ml. Solutions of arginase I and II are prepared in 100 mM sodium phosphate buffer, pH 7.4 containing 1 mg/ml of OVA to give an arginase stock solution at a final concentration of 100 ng/ml.

To each well of a 96-well microtiter plate is add 40 µl of enzyme, 10 µl of an inventive compound and 10 µl of enzyme substrate (L-arginine+manganese sulfate). For wells that are used as positive controls, only the enzyme and its substrate are added, while wells used as negative controls contain only manganese sulfate.

After incubating the microtiter plate at 37° C. for 60 minutes, 150 µl of a urea reagent obtained by combining equal proportions (1:1) of reagents A and B is added to each well of the microtiter plate to stop the reaction. The urea reagent is made just before use by combining Reagent A (10 mM o-phthaldialdehyde, and 0.4% polyoxyethylene (23) lauryl ether (w/v) in 1.8 M sulfuric acid) with Reagent B (1.3 mM primaquine diphosphate, 0.4% polyoxyethylene (23) lauryl ether (w/v), 130 mM boric acid in 3.6 M sulfuric acid). After quenching the reaction mixture, the microtiter plate is allowed to stand for an additional 10 minutes at room temperature to allow color development. The inhibition of arginase is computed by measuring the optical density (OD) of the reaction mixture at 530 nm and normalizing the OD value to percent inhibition observed in the control. The normalized OD is then used to generate a dose-response curve by plotting the the normalized OD values against log [concentration] and using regression analysis to compute the $IC_{50}$ values.

Table 3 below ranks the potency of inventive compounds on a scale from 1 through 5, that is, the most potent compounds are designated as 1 and the least potent compounds are designated as 5. Thus, a potency value of 1 refers to inventive compounds with $IC_{50}$ values in the range from 0.1 nM to 25 nM; a potency value of 2 refers to inventive compounds with $IC_{50}$ values in the range from 26 nM to 100 nM; compounds having a potency value of 3 exhibit $IC_{50}$ values in the range from 101 nM to 500 nM; inventive compounds with $IC_{50}$ values in the range from 501 nM to 1500 nM are assigned a potency value of 4, and compounds with $IC_{50}$ values above 1501 nM are assigned a potency value of 5.

TABLE 3

| Ex. # | Structure* | Name | [a]Arg I IC$_{50}$ | [a]Arg II IC$_{50}$ |
|---|---|---|---|---|
| 1 | 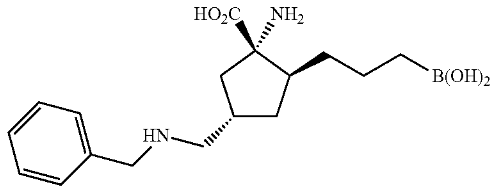 [SMILES: N[C@@]1(C(=O)O)C[C@@H](CNCc2ccccc2)C[C@@H]1CCCB(O)O] | (1S,2S,4S)-1-amino-4-((benzylamino)methyl)-2-(3-boronopropyl)cyclopentanecarboxylic acid | 2 | 2 |
| 2 | 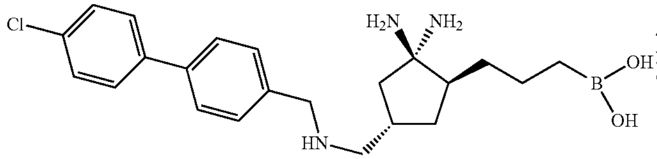 | (1S,2S,4S)-1-amino-2-(3-boronopropyl)-4-((((4'-chloro-[1,1'-biphenyl]-4-yl)methyl)amino)methyl)cyclopentane-carboxylic acid | 2 | 2 |
| 3 | 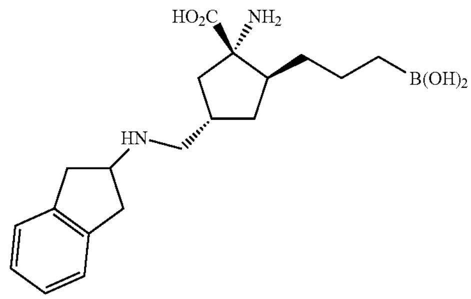 [SMILES: N[C@@]1(C(=O)O)C[C@@H](CNC2Cc3ccccc3C2)C[C@@H]1CCCB(O)O] | (1S,2S,4S)-1-amino-2-(3-boronopropyl)-4-(((2,3-dihydro-1H-inden-2-yl)amino)methyl)cyclopentanecarboxylic acid | 2 | 3 |
| 4 | 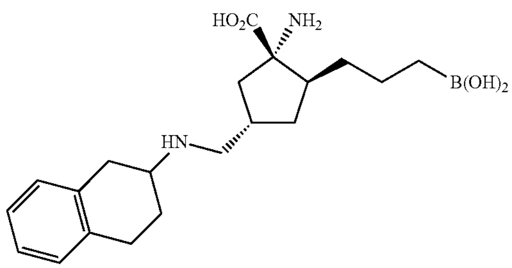 [SMILES: N[C@@]1(C(=O)O)C[C@@H](CNC2CCc3ccccc3C2)C[C@@H]1CCCB(O)O] | (1S,2S,4S)-1-amino-2-(3-boronopropyl)-4-(((1,2,3,4-tetrahydronaphthalen-2-yl)amino)methyl)cyclopentanecarboxylic acid | 2 | 2 |
| 5 | 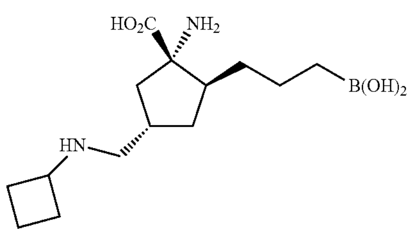 [SMILES: N[C@@]1(C(=O)O)C[C@@H](CNC2CCC2)C[C@@H]1CCCB(O)O] | (1S,2S,4S)-1-amino-2-(3-boronopropyl)-4-((cyclobutylamino)methyl)cyclopentane-carboxylic acid | 2 | 3 |
| 6 | 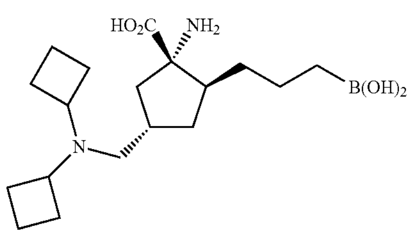 [SMILES: N[C@@]1(C(=O)O)C[C@@H](CN(C2CCC2)C2CCC2)C[C@@H]1CCCB(O)O] | (1S,2S,4S)-1-amino-2-(3-boronopropyl)-4-((dicyclobutylamino)methyl)cyclopentane-carboxylic acid | 3 | 3 |
| 7 | 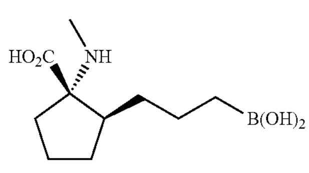 [SMILES: CN[C@@]1(C(=O)O)CCC[C@@H]1CCCB(O)O] | (1S,2)S-2-(3-boronopropyl)-1-(methylamino)cyclopentanecarboxylic acid | 4 | 4 |

TABLE 3-continued

| Ex. # | Structure* | Name | [a]Arg I IC$_{50}$ | [a]Arg II IC$_{50}$ |
|---|---|---|---|---|
| 8 | H$_2$N, CO$_2$H / cyclopentane / B(OH)$_2$ | (1S,2S)-1-amino-2-(3-boronopropyl)cyclopentanecarboxylic acid | 3 | 3 |
| 9 | H$_2$N, CO$_2$H / pyrrolidine / B(OH)$_2$ | (3R,4S)-3-amino-4-(3-boronopropyl)pyrrolidine-3-carboxylic acid | 3 | 3 |

[a]Order of Potency (highest-lowest): 1 = 0.1 nM → 25 nM; 2 = 26 nM → 100 nM; 3 = 101 nM → 500 nM; 4 = 501 nM → 1500 nM; and 5 = 1501 nM → greater.

The foregoing examples are intended illustrate certain embodiments of the invention, which is defined in full below by the claims. In addition, all publications cited herein are incorporated by reference as if fully set forth herein.

We claim:

1. A compound that is selected from the following table:

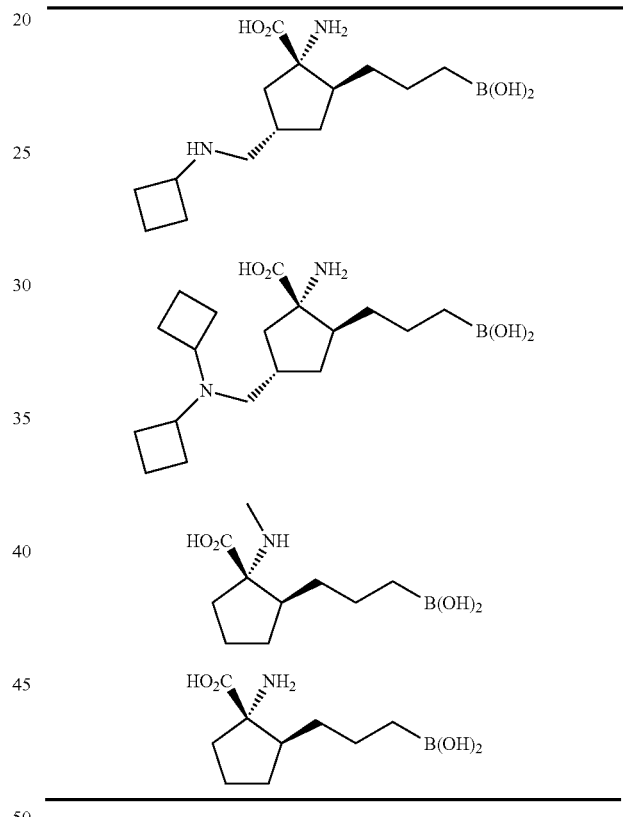

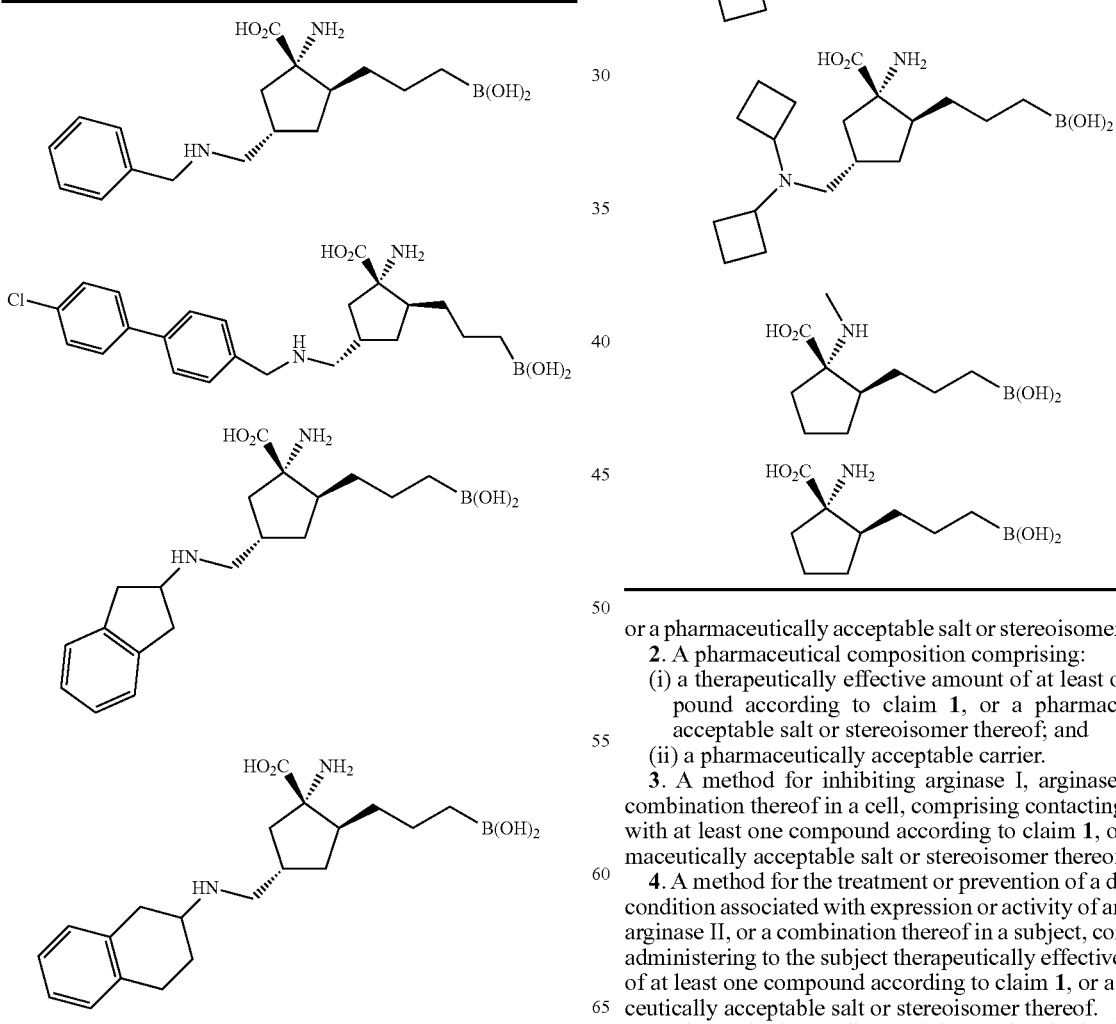

or a pharmaceutically acceptable salt or stereoisomer thereof.

2. A pharmaceutical composition comprising:
   (i) a therapeutically effective amount of at least one compound according to claim 1, or a pharmaceutically acceptable salt or stereoisomer thereof; and
   (ii) a pharmaceutically acceptable carrier.

3. A method for inhibiting arginase I, arginase II, or a combination thereof in a cell, comprising contacting the cell with at least one compound according to claim 1, or a pharmaceutically acceptable salt or stereoisomer thereof.

4. A method for the treatment or prevention of a disease or condition associated with expression or activity of arginase I, arginase II, or a combination thereof in a subject, comprising administering to the subject therapeutically effective amount of at least one compound according to claim 1, or a pharmaceutically acceptable salt or stereoisomer thereof.

5. The method according to claim 4, wherein the disease or condition is selected from cardiovascular disorders, sexual disorders, wound healing disorders, gastrointestinal disorders, autoimmune disorders, immune disorders, infections, pulmonary disorders and hemolytic disorders.

6. The method according to claim 5, wherein the disease or condition is cardiovascular disorder selected from systemic hypertension, pulmonary arterial hypertension (PAH), pulmonary arterial hypertension in high altitude, ischemia reperfusion (IR) injury, myocardial infarction, and atherosclerosis.

7. The method according to claim 6, wherein the disease or condition is pulmonary arterial hypertension (PAH).

8. The method according to claim 6, wherein the disease or condition is myocardial infarction or atherosclerosis.

9. The method according to claim 5, wherein the disease or condition is a pulmonary disorder selected from chemically-induced lung fibrosis, idiopathic pulmonary fibrosis, cystic fibrosis, chronic obstructive pulmonary disease (COPD), and asthma.

10. The method according to claim 5, wherein the disease or condition is an autoimmune disorder selected from encephalomyelitis, multiple sclerosis, anti-phospholipid syndrome 1, autoimmune hemolytic anaemia, chronic inflammatory demyelinating polyradiculoneuropathy, dermatitis herpetiformis, dermatomyositis, myasthenia gravis, pemphigus, rheumatoid arthritis, stiff-person syndrome, type 1 diabetes, ankylosing spondylitis, paroxysmal nocturnal hemoglobinuria (PNH), paroxysmal cold hemoglobinuria, severe idiopathic autoimmune hemolytic anemia, and Goodpasture's syndrome.

11. The method according to claim 5, wherein the disease or condition is an immune disorder selected from myeloid-derived suppressor cell (MDSC) mediated T-cell dysfunction, human immunodeficiency virus (HIV), autoimmune encephalomyelitis, and ABO mismatch transfusion reaction.

12. The method according to claim 11, wherein the disease or condition is myeloid-derived suppressor cell (MDSC) mediated T-cell dysfunction.

13. The method according to claim 5, wherein the disease or condition is a hemolytic disorder selected from sickle-cell disease, thalassemias, hereditary spherocytosis, stomatocytosis, microangiopathic hemolytic anemias, pyruvate kinase deficiency, infection-induced anemia, cardiopulmonary bypass and mechanical heart valve-induced anemia, and chemical induced anemia.

14. The method according to claim 5, wherein the disease or condition is a gastrointestinal disorder selected from gastrointestinal motility disorders, gastric cancers, inflammatory bowel disease, Crohn's disease, ulcerative colitis, and gastric ulcers.

15. The method according to claim 5, wherein the disease or condition is a sexual disorder selected from Peyronie's Disease and erectile dysfunction.

16. The method according to claim 5, wherein the disease or condition is ischemia reperfusion (IR) injury selected from liver IR, kidney IR, and myocardial IR.

17. The method according to claim 4, wherein the disease or condition is selected from renal disease inflammation, psoriasis, leishmaniasis, neurodegenerative diseases, wound healing, human immunodeficiency virus (HIV), hepatitis B virus (HBV), H. pylori infections, fibrotic disorders, arthritis, candidiasis, periodontal disease, keloids, adenotonsillar disease, African sleeping sickness and Chagas' disease.

18. The method according to claim 5, wherein the disease or condition is a wound healing disorder selected from infected and uninfected wound healing.

19. The method according to claim 4, wherein the subject is a mammal selected from human, dog, cat, horse, cow, sheep, and lamb.

* * * * *